US007767872B2

(12) United States Patent
Acey et al.

(10) Patent No.: US 7,767,872 B2
(45) Date of Patent: *Aug. 3, 2010

(54) THIMEROSAL REMOVAL DEVICE

(75) Inventors: Roger A. Acey, Long Beach, CA (US); Richard Clinton Kanner, Santa Ana, CA (US)

(73) Assignee: MPG Biotechnologies, LLC, Irvine, CA (US)

( * ) Notice: Subject to any disclaimer, the term of this patent is extended or adjusted under 35 U.S.C. 154(b) by 386 days.

This patent is subject to a terminal disclaimer.

(21) Appl. No.: 11/624,059

(22) Filed: Jan. 17, 2007

(65) Prior Publication Data

US 2007/0160599 A1 Jul. 12, 2007

Related U.S. Application Data

(60) Continuation-in-part of application No. 11/255,427, filed on Oct. 19, 2005, now Pat. No. 7,273,962, and a continuation-in-part of application No. 10/797,748, filed on Mar. 9, 2004, now Pat. No. 7,135,605, which is a division of application No. 09/948,495, filed on Sep. 6, 2001, now Pat. No. 6,750,056.

(60) Provisional application No. 60/759,671, filed on Jan. 17, 2006, provisional application No. 60/620,528, filed on Oct. 19, 2004.

(51) Int. Cl.
*A62D 3/00* (2007.01)
*C07K 14/00* (2006.01)

(52) U.S. Cl. ................ 588/315; 588/412; 530/300; 514/2

(58) Field of Classification Search ........... None
See application file for complete search history.

(56) References Cited

U.S. PATENT DOCUMENTS

| | | | |
|---|---|---|---|
| 3,948,266 A | 4/1976 | Clark et al. | |
| 4,083,368 A | 4/1978 | Freezer | |
| 4,342,310 A | 8/1982 | Lindmayer et al. | |
| 5,154,833 A | 10/1992 | Robinson | |
| 5,263,475 A | 11/1993 | Altermatt et al. | |
| 5,441,643 A | 8/1995 | Spears et al. | |
| 5,500,353 A | 3/1996 | Smit et al. | |
| 5,520,639 A | 5/1996 | Peterson et al. | |
| 5,567,316 A | 10/1996 | Spears et al. | |
| 5,571,246 A | 11/1996 | Alldredge | |
| 5,665,865 A | 9/1997 | Lerner et al. | |
| 5,679,548 A | 10/1997 | Barbas et al. | |
| 5,814,480 A | 9/1998 | Hillman et al. | |
| 5,824,512 A | 10/1998 | Pazirandeh et al. | |
| 5,860,416 A | 1/1999 | Howlett | |
| 5,993,412 A | 11/1999 | Deily et al. | |
| 6,131,566 A | 10/2000 | Ashurst et al. | |
| 6,345,617 B1 | 2/2002 | Engelbreth et al. | |
| 6,391,590 B1 | 5/2002 | Sano et al. | |
| 6,451,260 B1 | 9/2002 | Dusterhoft et al. | |
| 6,471,669 B2 | 10/2002 | Landau | |
| 6,557,550 B1 | 5/2003 | Clarke | |
| 6,745,761 B2 | 6/2004 | Christrup et al. | |
| 6,750,042 B2 | 6/2004 | Summers et al. | |
| 6,939,323 B2 | 9/2005 | Angel et al. | |
| 6,955,169 B2 | 10/2005 | Khan | |
| 7,007,689 B2 | 3/2006 | Burns | |
| 7,029,457 B2 | 4/2006 | Rogatchev et al. | |
| 7,032,594 B2 | 4/2006 | Newton et al. | |
| 7,047,967 B2 | 5/2006 | Knudsen | |
| 7,056,300 B2 | 6/2006 | Alexandre et al. | |
| 7,077,130 B2 | 7/2006 | Nichols et al. | |
| 7,135,605 B2 * | 11/2006 | Acey et al. ............ | 588/315 |
| 7,143,764 B1 | 12/2006 | Dagsland et al. | |
| 7,150,409 B2 | 12/2006 | Gonnelli et al. | |
| 7,156,822 B2 | 1/2007 | Navelier et al. | |
| 7,273,962 B2 * | 9/2007 | Acey ................ | 588/315 |
| 2003/0105304 A1 | 6/2003 | Acey et al. | |

FOREIGN PATENT DOCUMENTS

| | | |
|---|---|---|
| EP | 0557042 | 6/1993 |
| JP | 2003082422 | 3/2003 |
| WO | 03022868 | 3/2003 |
| WO | 2006/045103 A | 4/2006 |

OTHER PUBLICATIONS

Hamer, Metallothionein. Annual Review of Biochemistry, 1986, pp. 913-951, vol. 55.
Fischer, et al., Recent excitement regarding metallothionein, Proceedings of the National Academy of Sciences, 1998, pp. 333-334, vol. 95.
Evanko, et al., Remediation of Metals—Contaminated Soils and Groundwater, Technology Evolution Report for GWRTAC, 1997, pp. i-53.
Pedersen, et al., Primary structures of decapod crustacean metallothioneins with special emphasis on freshwater and semi-terrestrial species, Biochemistry Journal, 1996, pp. 999-1003, vol. 319.
Rudinger, "Characteristics of the amino acids as componants of a peptide hormone sequence" in Peptide Hormones, pp. 1-7, University Park Press: Baltimore, MD, Parsons Edition, Jun. 1976.
Kennell, Principles and practices of nucleic acid hybridization, Progr. Nucleic Acid Res. Mol. Biol., 1971, pp. 259-301, vol. 11.
Ngo, et al., "Computational complexity, protein structure prediction, and the Levinthal paradox" in The Protein Folding Problem and Tertiary Structure Prediction, 1994, pp. 492-495, Birkhauser Boston: Boston, MA, Mertz et al Edition.
Chen, et al., HG2+ removal by genetically engineered *Escherichia coli* in a hollow fiber reactor, Biotechnology Progress, 1998, pp. 667-671, vol. 14.

(Continued)

*Primary Examiner*—Anand U Desai
(74) *Attorney, Agent, or Firm*—Louis C. Cullman; Michelle Glasky Bergman; K&L Gates LLP

(57) ABSTRACT

A device for the removal of heavy metals and heavy metal complexes, such as thimerosal, from medications is provided wherein the device comprises a dosing device or a solid support having at least one substantially purified metallothionein protein associated therewith. Additionally, methods to remove thimerosal from medications are provided.

24 Claims, 12 Drawing Sheets

OTHER PUBLICATIONS

Bae, et al., Enhanced bioaccumulation of heavy6 metals by bacterial cells displaying synthetic phytochelatins, Biotechnology and Bioengineering, 2000, pp. 518-524, vol. 70, No. 5.

Ma, et al., Recent Developments for in Situ Treatment of Metal contaminated Soils, Prepared for U.S. EPA by PRC Management, Inc., 1997 and published on web site at www.clu-in.org//download/remed/metals2.pdf.

Chen, et al., The induction and extraction of metallothioneins in Artemia, Chinese Journal of Oceanography and Limnology, 1994, pp. 175-179, vol. 12, No. 2.

Valls, et al., Engineering a mouse metallothionein on the cell surface of *Ralstonia europha* CH34 for immobilization of heavy metals in soil, Nature Biotechnology, 2000, pp. 661-665, vol. 18.

Del Ramo, et al, Effect of cadmium pre-exposure in cadmium accumulation by brine shrimp *Artemia*: involvement of low-molecular-weight cadmium-binding ligands, Marine Environmental Research, 1993, pp. 29-33, vol. 5.

Sode, et al., Construction of a marine cyanobacterial strain with increased heavy metal ion tolerance by introducing exogenous metallothionein gene, Journal of Marine Biotechnology, 1998, pp. 174-177, vol. 6.

Brook, et al., Purification of metallothionein-like metal binding proteins from *Artemia*, Molecular Biology of the Cell, 1994, p. 226A, Abstract No. 1316, vol. 5.

Offit Pa et al., Addressing parents' concerns: Do vaccines contain harmful preservatives, adjuvants, additives or residuals. Pediatrics. 112:1394-1397, 2003.

\* cited by examiner

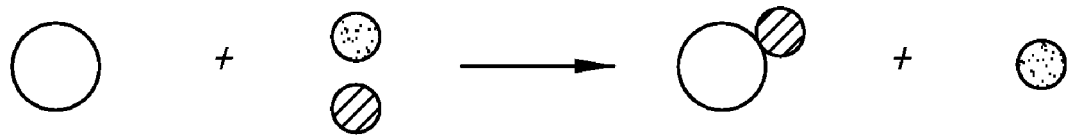
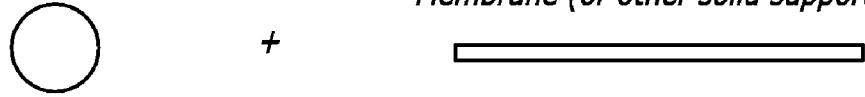
FIG. 2
FIG. 3

FIG. 6

```
                      (1)   1         10        20        30        40
           Artemia    (1)   ---------------MDCCK-----NGCTCA-PNCKCA-------
            Rabbit    (1)   ------------MDP-NCSCA-TRDSCACA-SSCKCKE------
             Human    (1)   ------------MDP-NCSCA-AGDSCTCA-GSCKCKE------
      Green Monkey    (1)   ------------MDP-NCSCA-TGVSCTCA-DSCKCKE------
   Channel Catfish    (1)   ------------MDP--CECS-KTGTCNCG-TSCKCSN------
African Clawed Frog   (1)   ------------MDPQDCKCE-TGASCSCG-TTCSCSN------
       Blue Mussel    (1)   PGPCNCIETNVCICGTG-CS-G---KCCRCG-DACKCA-------
 Painted Sea Urchin   (1)   -----------MPGPDVKCFCCRDGKECACGGGECCITG------
         Fruit Fly    (1)   --------------------------MVCK--GCGTN-------
         C. elegans   (1)   ----------------VCK-------CDCKNQNCSCNTGT----
              Rice    (1)   ---------------MSCSCG---SSCSCG-SNCSCGKKYPDLE
             Wheat    (1)   ---------------MSCNCG---SGCSCG-SDCKCGKMYPDLT
             Yeast    (1)   ANDCKCPN----GCSCPNCA-N---GGCQCG-DKCECK-------

(46)  46        60        70        80
           Artemia   (46)  KDCKC-----CKG-CECKSNPECK---------CEKNCS------
            Rabbit   (46)  --CKCTSCKKSCCSCCPAGCTKCA---------QGCICKG-----
             Human   (46)  --CKCTSCKKSCCSCCPVGCAKCA---------QGCICKG-----
      Green Monkey   (46)  --CKCTSCKKSCCSCCPVGCAKCA---------QGCVCKG-----
   Channel Catfish   (46)  --CQCACCKKSCCSCCPSGCSKCA---------SGCVCKG-----
African Clawed Frog  (46)  --CKCTSCKKSCCSCCPAECSKCS---------QGCHCEK-----
       Blue Mussel   (46)  SGCGCSG---CKVVCKCS--GTCK---------CGCDCTGPT-NC
 Painted Sea Urchin  (46)  --KCCKEGDRTCCGKCSNAACKCA---------DGCKCEGA--CA
         Fruit Fly   (46)  --CQCSAQKCGDNCACNKDC-------------QCVCKN-----
         C. elegans  (46)  KDCDCSDAKCCEQYCCPTASEKKC---------CKSGCAG---GC
              Rice   (46)  EKSSSTK---ATVVLGVAPEKKAQ--QFEAAAESGETAHGCS---
             Wheat   (46)  EQGSAAAQVAAVVVLGVAPENKAG--QFEVAA--GQSGEGCS---
             Yeast   (46)  -KQSCIIG---CGEQCKCGS---------------IIGSSCIIG---SC

(91)  91        100       110
           Artemia   (91)  -CNS-CGCII------------------   SEQ ID NO. 11
            Rabbit   (91)  -ALDKCSCCA------------------   SEQ ID NO. 12
             Human   (91)  -ASDKCSCCA------------------   SEQ ID NO. 13
      Green Monkey   (91)  -ASEKCNCCA------------------   SEQ ID NO. 14
   Channel Catfish   (91)  -DTCDSKCCQ------------------   SEQ ID NO. 15
African Clawed Frog  (91)  -GSKKCSCCN------------------   SEQ ID NO. 16
       Blue Mussel   (91)  KCESGCSCK-------------------   SEQ ID NO. 17
 Painted Sea Urchin  (91)  CTMGNCTC--------------------   SEQ ID NO. 18
         Fruit Fly   (91)  --GPKDQCCSNK----------------   SEQ ID NO. 19
         C. elegans  (91)  KCAN-CECAQ--------------AAH   SEQ ID NO. 20
              Rice   (91)  -CGSSCRCNPCNC---------------   SEQ ID NO. 21
             Wheat   (91)  -CGDNCKCNPCNC---------------   SEQ ID NO. 22
             Yeast   (91)  GCGDKCECK-------------------   SEQ ID NO. 23
```

THIMEROSAL REMOVAL DEVICE

CROSS REFERENCE TO RELATED APPLICATIONS

The present application claims the benefit under 35 U.S.C. §119(e) to U.S. Provisional Patent Application No. 60/759,671 filed Jan. 17, 2006 and is a continuation-in-part of U.S. patent application Ser. No. 11/255,427 filed Oct. 19, 2005, now U.S. Pat. No. 7,273,962, which in turn claims priority to U.S. Provisional Patent Application No. 60/620,528 filed Oct. 19, 2004 and is a continuation-in-part of U.S. patent application Ser. No. 10/797,748, filed Mar. 9, 2004, now U.S. Pat. No. 7,135,605 which is a divisional of U.S. patent application Ser. No. 09/948,495 filed Sep. 6, 2001, now U.S. Pat. No. 6,750,056, the entire contents of which are incorporated by reference herein in their entirety.

FIELD OF THE INVENTION

The present invention relates to compositions and methods for removing heavy metals and heavy metal complexes from biological materials. More specifically the present invention relates to removing thimerosal from bioactive materials intended to be administered to patients at the time of administration using metallothionein proteins associated with dosing devices.

BACKGROUND OF THE INVENTION

Thimerosal, which is approximately 50% mercury by weight, has been one of the most widely used preservatives in vaccines. It is metabolized or degraded to ethylmercury and thiosalicylate. Ethylmercury is an organomercurial that should be distinguished from methylmercury, a related substance that has been the focus of considerable study.

At concentrations found in vaccines, thimerosal meets the requirements for a preservative as set forth by the *United States Pharmacopeia*; that is, it kills the specified challenge organisms and is able to prevent the growth of the challenge fungi (U.S. Pharmacopeia 2004). Thimerosal in concentrations of 0.001% (1 part in 100,000) to 0.01% (1 part in 10,000) has been shown to be effective in clearing a broad spectrum of pathogens. A vaccine containing 0.01% thimerosal as a preservative contains 50 micrograms of thimerosal per 0.5 mL dose or approximately 25 micrograms of mercury per 0.5 mL dose.

Thimerosal is a mercury-containing organic compound (an organomercurial). Since the 1930s, it has been widely used as a preservative in a number of biological and drug products, including many vaccines, to help prevent potentially life threatening contamination with harmful microbes. Over the past several years, because of an increasing awareness of the theoretical potential for neurotoxicity of even low levels of organomercurials, concerns about the use of thimerosal in vaccines and other products have been raised. Indeed, because of these concerns, the United States Food and Drug Administration (FDA) has worked with, and continues to work with, vaccine manufacturers to reduce or eliminate thimerosal from vaccines.

Thimerosal has been removed from or reduced to trace amounts in all vaccines routinely recommended for children 6 years of age and younger, with the exception of inactivated influenza vaccine. Some vaccines such as Td (tetanus and diphtheria vaccine), which is indicated for older children ($\geq 7$ years of age) and adults, are also now available in formulations that are free of thimerosal or contain only trace amounts. Vaccines with trace amounts of thimerosal contain 1 microgram or less of mercury per dose.

The various mercury guidelines are based on epidemiological and laboratory studies of methyl mercury, whereas thimerosal is a derivative of ethyl mercury. Because they are different chemical entities—ethyl-versus methylmercury—different toxicological profiles are expected. There is, therefore, an uncertainty that arises in applying the methylmercury-based guidelines to thimerosal. Lacking definitive data on the comparative toxicities of ethyl-versus methylmercury, the FDA considered ethyl- and methyl-mercury as equivalent in its risk evaluation.

Allergic responses to thimerosal are described in the clinical literature, with these responses manifesting themselves primarily in the form of delayed-type local hypersensitivity reactions, including redness and swelling at the injection site (Cox NH, Forsyth A. Thimerosal allergy and vaccination reactions. Contact Dermatitis 18:229-233, 1988). Such reactions are usually mild and last only a few days.

In 2001, the Institute of Medicine (IOM) convened a committee (the Immunization Safety Review Committee) to review selected issues related to immunization safety. One such review focused on a potential relationship between thimerosal use in vaccines and neurodevelopmental disorders (Institute of Medicine, Thimerosal-containing vaccines and neurodevelopmental disorders, Washington D.C.: National Academy Press, 2001). In its report, the IOM's Immunization Safety Review Committee concluded that the evidence was inadequate to either accept or reject a causal relationship between thimerosal exposure from childhood vaccines and the neurodevelopmental disorders of autism, attention deficit hyperactivity disorder (ADHD), and speech or language delay. Additional studies were needed to establish or reject a causal relationship. The Committee did conclude that the hypothesis that exposure to thimerosal-containing vaccines could be associated with neurodevelopmental disorders was biologically plausible.

Therefore there exists a need for methods and systems to easily remove thimerosal from injectable materials at the point of service.

Metallothioneins (MTs) are small metal binding proteins ubiquitously distributed throughout the animal kingdom. They have high metal binding affinities and are believed to be important in controlling the intracellular levels of free metal ions. The structural features of MTs include a high cysteine composition and lack of aromatic amino acids. The cysteine residues are responsible for the protein's high affinity metal binding to heavy metals including arsenic, zinc, copper, cadmium, mercury, cobalt, lead, nickel, chromium, uranium, platinum, gold, silver and their complexes. In general, MTs from divergent species have a high degree of amino acid sequence similarity. If fact, the amino acid residues responsible for metal binding are essentially invariant between species.

Accordingly, an object of the present invention is to provide methods and devices to remove thimerosal from medications and bioactive materials at the time of administration using metallothionein-based systems.

SUMMARY OF THE INVENTION

Devices and methods for removing metals, such as mercury-containing thimerosal, from medications and bioactive materials using metallothionein proteins are provided.

In one embodiment of the present invention, a device for the removal of thimerosal from a medication to be administered to a subject is provided comprising a dosing device having associated therewith at least one substantially purified metallothionein protein, wherein the at least one substantially purified metallothionein protein binds thimerosal from the medication resulting in a substantially thimerosal-free medication.

In another embodiment, the dosing device is selected from the group consisting of syringes, oral dosing syringes, oral dosing cups, inhalation devices, needles, needleless injection devices and ophthalmologic administrative devices. In another embodiment, the dosing device provides a sterile environment.

In another embodiment, administration comprises a route of administration selected from the group consisting of intravenous injection, subcutaneous injection, intradermal injection, intramuscular injection, intravenous infusion, oral, inhalation, and intraocular. In another embodiment, the medication is selected from the group consisting of vaccines, immunogenic compositions, liquid pharmaceutical compositions, colloidal pharmaceutical compositions, suspension pharmaceutical compositions, aerosols and dry powders.

In another embodiment of the present invention, the dosing device removes thimerosal from the medication proximal in time to the administration. In another embodiment, at least one interior surface of the dosing device has at least one substantially pure metallothionein protein coated thereon. In another embodiment, the at least one substantially pure metallothionein protein is covalently linked to the interior surface. In another embodiment, the at least one substantially pure metallothionein protein is coated on interior surface in a polymeric coating.

In another embodiment of the present invention, the at least one substantially pure metallothionein protein is bound to a solid support, the solid support associated with the dosing device. In another embodiment, the at least one substantially pure metallothionein protein is bound to a solid support, the solid support disposed within the dosing device.

In an embodiment of the present invention, the solid support is selected from the group consisting of filters, membranes, nanoparticles, beads, solid support particulates, and polymer coatings. In another embodiment, the at least one substantially pure metallothionein protein is associated with a plurality of beads or nanoparticles, the plurality of beads or nanoparticles disposed within the dosing device. In another embodiment, the solid support comprises a biocompatible polymer. In another embodiment, the biocompatible polymer is selected from the group consisting of fluorinated polymers, polyolefins, polystyrene, substituted polystyrenes, polysulfones, polyesters, polyacrylates, polycarbonates; vinyl polymers, copolymers of butadiene and styrene, fluorinated ethylene-propylene copolymers, ethylenechlorotrifluoroethylene copolymers, nylon and mixtures thereof. In another embodiment, the solid support is a filter.

In another embodiment of the present invention, the at least one substantially purified metallothionein (MT) protein, or a portion thereof, is from an organism selected from the group consisting of mammals, fish, mollusks, echinoderms, crustaceans, reptiles, nematodes, grains, plants, yeast, and fungi. In another embodiment, the mammal is a human. In another embodiment, the mammal is a rabbit. In another embodiment, the crustacean is brine shrimp (*Artemia*).

In another embodiment of the present invention, the MT protein has an amino acid sequence selected from the group consisting of SEQ ID NO. 2, SEQ ID NO. 4, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 21 and SEQ ID NO. 23.

In one embodiment of the present invention, a method is provided forf removing thimerosal from a medication to be administered to a subject comprising contacting a thimerosal-containing medication with at least one substantially purified metallothionein protein associated with a dosing device; and administering the resulting substantially thimerosal-free medication to the subject.

In an embodiment of the present invention, a system is provided for removing thimerosal from a medication to be administered to a subject comprising a device having at least one metallothionein protein associated therewith; wherein passage of a medication through the device results in binding of thimerosal to the metallothionein protein and a substantially thimerosal-free medication In an embodiment of the present invention, a device is provided for the removal of thimerosal from a medication to be administered to a subject comprising a solid support associated with at least one substantially purified metallothionein protein, wherein the at least one substantially purified metallothionein protein binds thimerosal from the medication resulting in a substantially thimerosal-free medication.

BRIEF DESCRIPTION OF THE DRAWINGS

FIG. 2 illustrates metallothionein (MT) protein selectively binding heavy metals in solution in accordance with the teachings of the present invention.

FIG. 3 illustrates MT proteins coupled to a solid support in accordance with the teachings of the present invention.

FIG. 6 depicts the sequence homology in the cysteine metal binding motifs between metallothionein proteins isolated from divergent species.

DETAILED DESCRIPTION OF THE INVENTION

A system, device and method for removing metals, such as mercury-containing thimerosal, from medications using metallothionein proteins are provided. In one embodiment, a dosing device is provided which removes substantially all of the thimerosal from the medication as part of the dosing procedure. In another embodiment, the thimerosal is removed prior to the dosing procedure.

The dosing devices, systems and methods of the present invention remove substantially all of the thimerosal from the medication. In one embodiment, greater than about 90% of the thimerosal is removed. In another embodiment, greater than about 91%, 92%, 93%, 94%, 95%, 96%, 97%, 98% or 99% of the thimerosal is removed. In another embodiment, the present invention produces medications having less than about 1 μg of thimerosal per dose of medication. In another embodiment, each dose of medication contains less than about 0.7 μg. In another embodiment, each dose of medication contains less than about 0.5 μg of thimerosal. In yet another embodiment, each dose of medication contains less than about 0.1 μg of thimerosal.

As used herein, the term "medication" refers to any pharmaceutical preparation to be administered to a subject and which contains a heavy metal or heavy metal-containing compound including, but not limited to, thimerosal. The term medication includes, but is not limited to, injectable medications such as, but not limited to vaccines, immunogenic compositions, gene therapy agents and any type of injectable agent, liquid pharmaceutical compositions, colloidal pharmaceutical compositions, suspension pharmaceutical compositions, aerosols and dry powders. For the purposes of this disclosure, medication and bioactive material are used interchangeably.

Metal binding proteins such as metallothioneins (MTs) that have been isolated from various species such as humans, mice, bacteria species, crabs, fish, yeast and chickens, are known to have very similar structural characteristics such as similar size (about 6.0-6.8 kDa), high amino acid sequence conservation, and a high percentage of cysteine residues in the proteins' total amino acid compositions (FIG. 6). It is the cysteine composition of these MTs that accounts for the protein's binding affinity for heavy metals including, but not limited to, arsenic, zinc, copper, cadmium, mercury, cobalt, lead, nickel, chromium, uranium, platinum, silver and gold. Unless otherwise stated, the term protein refers to proteins, polypeptides and peptides and includes metal binding domains. The MT proteins of the present invention also bind heavy metal complexes in which the heavy metals are associated with a protein or other molecule.

Figure 4:
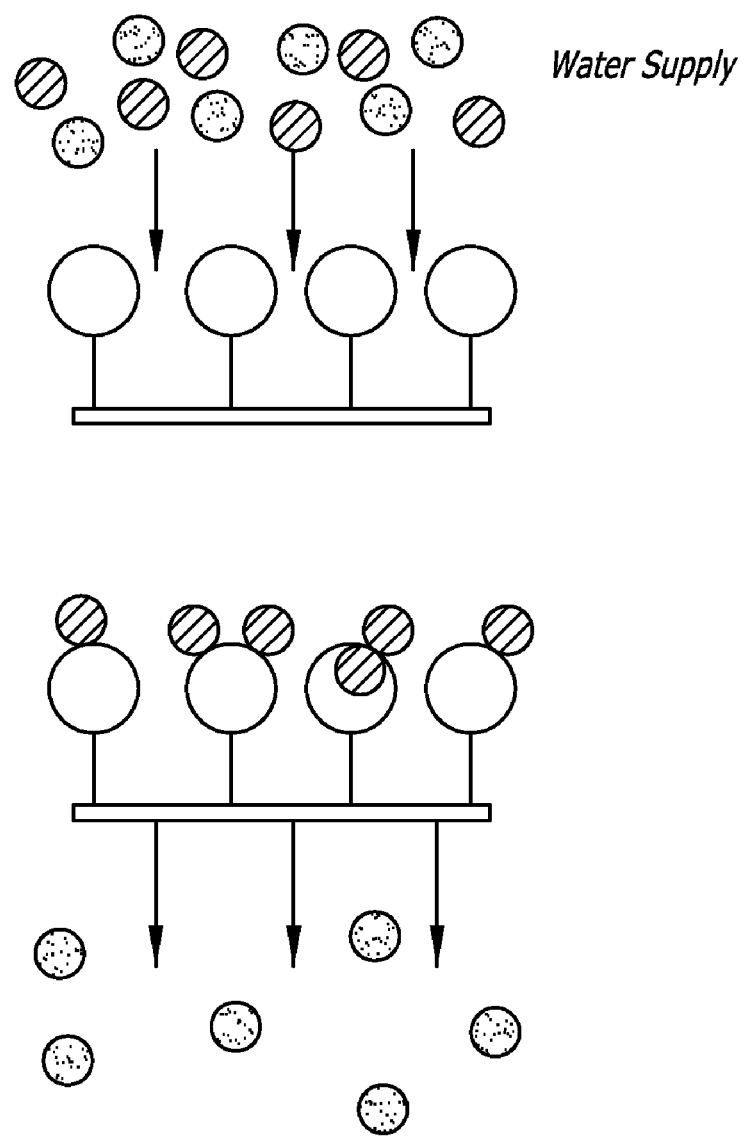
FIG. 4 illustrates the removal of heavy metals from water in accordance with the teachings of the present invention.

For example, the MT proteins, and devices comprising them disclosed herein are useful in connection with the treatment of any material having a concentration of at least one metal, such as a heavy metal or a heavy metal complexes, for example thimerosal. In particular, the MT proteins and devices of the present invention are useful for removing heavy metal containing complexes, such as the mercury-containing thimerosal, from injectable materials. Furthermore, MT proteins specifically bind certain heavy metals and do not bind other metals such as biologically required metals such as, but not limited to, calcium and magnesium (FIG. 2 and FIG. 4).

As used herein, medication is defined as any material suitable for administration to a mammal through any route. Non-limiting examples of medications include vaccines, plasma-derived products such as immune globulin and anti-toxins or anti-venoms and drugs including chemicals and biologicals including, but not limited to, proteins, peptides, hormones, polysaccharides, etc. Medications can also refer to immunogenic compositions, liquid pharmaceutical compositions, colloidal pharmaceutical compositions, suspension pharmaceutical compositions, aerosols and dry powders. Medication and bioactive material may be used interchangeably and are considered equivalent terms for the purposes of this disclosure. Routes of administration addressed by the devices and methods of the present invention include, but are not limited to, intravenous, subcutaneous, intradermal, and intramuscular injection; intravenous infusion; oral; inhalation; intraocular and other routes of administration known by medical professionals.

In general, a substrate from which one or more heavy metals or heavy metal complexes such as, but not limited to, thimerosal, are to be removed is contacted with an MT protein bound to a solid support, where the MT protein has an affinity for the heavy metal. The solid support forms a matrix to which the MT protein is irreversibly bound (FIG. 3).

The solid support can be in the form of a membrane, beads or solid support particulates, nanoparticles, a coating on a medical device or a dosing device, or any other form commonly used in biological or biochemical separations. If a membrane is used as the solid support, the MT-solid support composition can be incorporated into a contacting device comprising a housing, e.g., cartridge, containing the MT protein, by causing a solution containing a heavy metal to flow through an inlet port into the cartridge and thus come in contact with the MT protein before traveling out through an outlet port. In one embodiment, the inlet port and the outlet port can be the same port. Various housings may be used instead of a cartridge such as, but not limited to, a cassette, syringe, unit, canister, column or filter holder. Dosing devices include, but are not limited to, syringes, oral dosing syringes or cups, inhalation devices, needles and ophthalmologic administrative devices.

In one illustrative embodiment, the solid support is in the form of a membrane. Preferably, the membrane is a biocompatible polymer, and more preferably is a member selected from the group consisting of fluorinated polymers, polyolefins, polystyrene, substituted polystyrenes, polysulfones, polyesters, polyacrylates, polycarbonates; vinyl polymers, copolymers of butadiene and styrene, fluorinated ethylene-propylene copolymers, ethylenechlorotrifluoroethylene copolymers, nylon and mixtures thereof. In one embodiment, the membrane configuration is a pleated membrane, although other membrane configurations, such as flat sheet, mesh, pleated sheets, stacked disk, stacked sheets, and hollow fibers may be used as well as other configurations known to persons of ordinary skill in the art. A detailed discussion of solid supports, methods of binding MT proteins to solid supports and their use are disclosed in co-pending U.S. patent application Ser. No. 11/255,427, which is incorporated by reference for all it contains regarding MT proteins and solid supports.

Figure 7C:
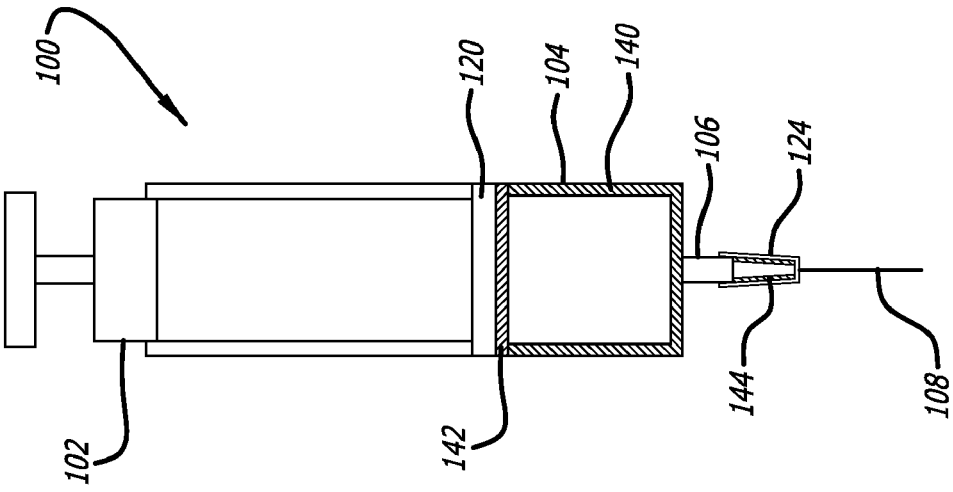
FIGS. 7A-C illustrates three embodiments of a thimerosal removal device of the present invention in the form of syringe dosing devices.
Figure 7B:
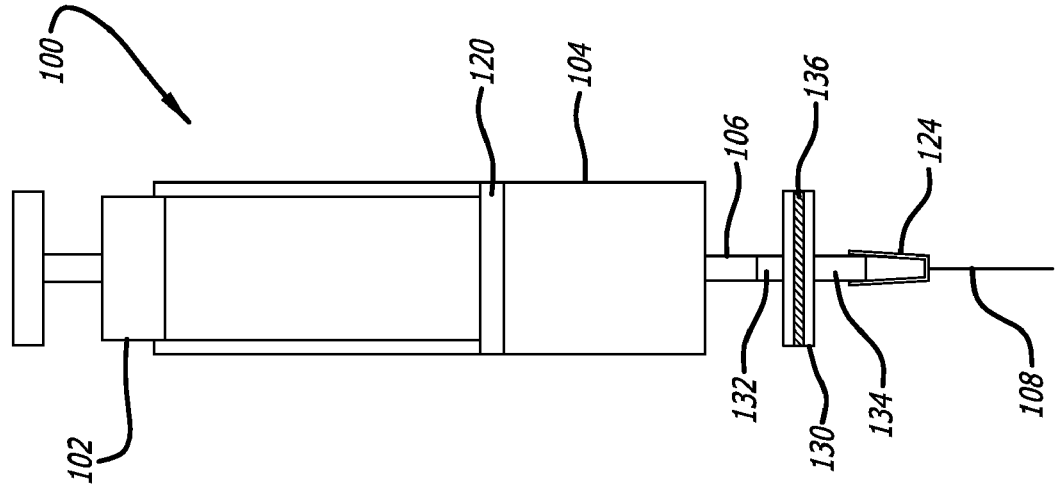
Figure 7A:
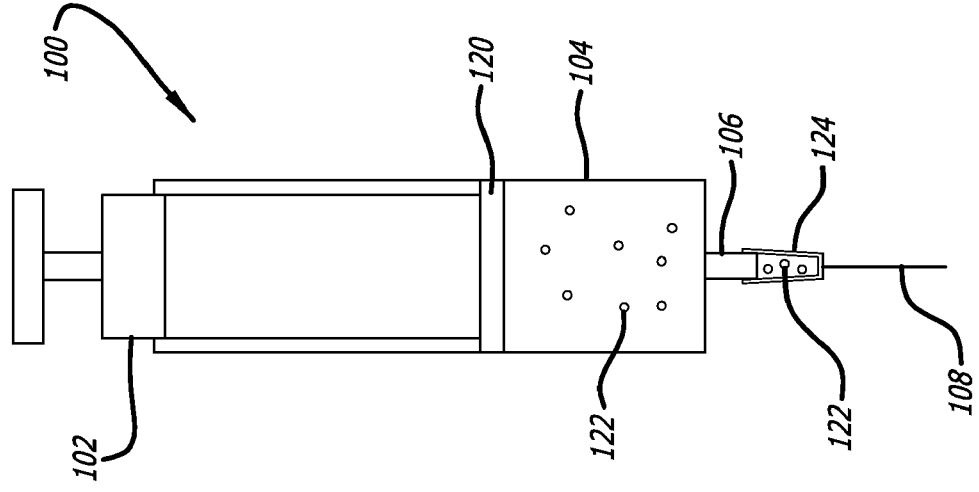

In one embodiment of the present invention, a dosing device has MT associated therewith to remove thimerosal from a thimerosal-containing solution passing through the dosing device. One exemplary dosing device depicted in FIG. 7 is a syringe. The MT can be associated with the dosing device in several ways. FIG. 7 depicts a syringe 100 generally having a plunger 102, a barrel 104 and a luer tip 106 for attachment to a needle 108. Needle 108 typically has a complimentary luer hub 124 for attaching to luer tip 106. Syringes can be manufactured to a variety of specifications and can have more or less components than depicted in FIG. 7. Optionally a gasket 120 is present to provide a seal between plunger 102 and barrel 104. In FIG. 7A, MT is bound to a solid support in the form of a bead 122, and a plurality of beads 122 having at least one MT protein bound thereto are disposed within barrel 104 of syringe 100 and/or luer hub 124 of needle 108 prior to a thimerosal-containing solution entering syringe 100. Injectable materials drawn into syringe 100 contact MT-coated beads 122 and thimerosal in the injectable material becomes bound to the MT protein. The beads can be of any size or shape compatible with their use. Beads useful within the luer hub 124 of needle 108 may be of a different size than those used within a reservoir or syringe barrel 104. Furthermore, beads within the barrel 104 of syringe 100 or luer hub 124 of needle 108 are retained within the barrel 104 or luer hub 124 after passage of the injectable material and do not pass into the subject or patient. The beads are retained by means including, but not limited to, presence of a membrane or mesh in barrel 104 or luer hub 124 with pore sizes smaller than the beads and/or the size of the beads exceeding the size of any exit ports of the barrel 104 or luer hub 124 such that the beads do not leave the barrel 104 or luer hub 124 with the injection material.

Beads suitable for coating with MT proteins include, but are not limited to, biocompatible polymers such as fluorinated polymers, polyolefins, polystyrene, substituted polystyrenes, polysulfones, polyesters, polyacrylates, polycarbonates; vinyl polymers, copolymers of butadiene and styrene, fluorinated ethylene-propylene copolymers, ethylenechlorotrifluoroethylene copolymers, nylon and mixtures thereof.

In yet another embodiment of a dosing device, MT is coated on a solid support is in the form of a filter. Filters with molecular weight cut offs sufficiently large to allow the injectable material to pass through are suitable for use in the present invention. FIG. 7B depicts a syringe 100 having disposed between luer tip 106 of syringe 100 and luer hub 124 of needle 108 a filter housing 130. At least one substantially pure MT protein is covalently bound to the biocompatible filter 136 contained within filter housing 130. An exemplary filter housing comprises a biocompatible plastic with an inlet port 132 and an outlet port 134 and a filter 136 disposed within the filter housing 130 having MT proteins bound thereto. The inlet port 134 and outlet port 136 have luer lock configurations to allow filter housing 130 to attach to syringe 100 and to needle 108. Preferable the filter housing 130 and filter 136 are stable to sterilization.

In still another embodiment, the solid support is in the form of a coating on the interior of the dosing device. In FIG. 7C, additional embodiments of a syringe dosing device are depicted. In non-limiting example, the interior of barrel 104 of syringe 100 is coated with a polymeric coating 140 to which at least one MT protein is bound. In another embodiment, the interior portion of luer hub 124 of needle 108 is coated with a polymeric coating 140 to which at least one MT protein is bound or incorporated therein. In yet another embodiment, the surface of rubber gasket 120 is coated with a polymeric coating 142 to which at least one MT protein is bound. In another embodiment, the interior of luer hub 124 of needle 108 is coated with a polymeric coating 144 to which at least one MT protein is bound. Injecteable materials containing thimerosal pass through barrel 104 and luer tip 106 of syringe 100 and luer hub 124 of needle 108 and thimerosal in the injectable material binds to the MT protein such that a substantial amount of the thimerosal is removed from the injectable material prior to entering the patient.

Figure 8A:
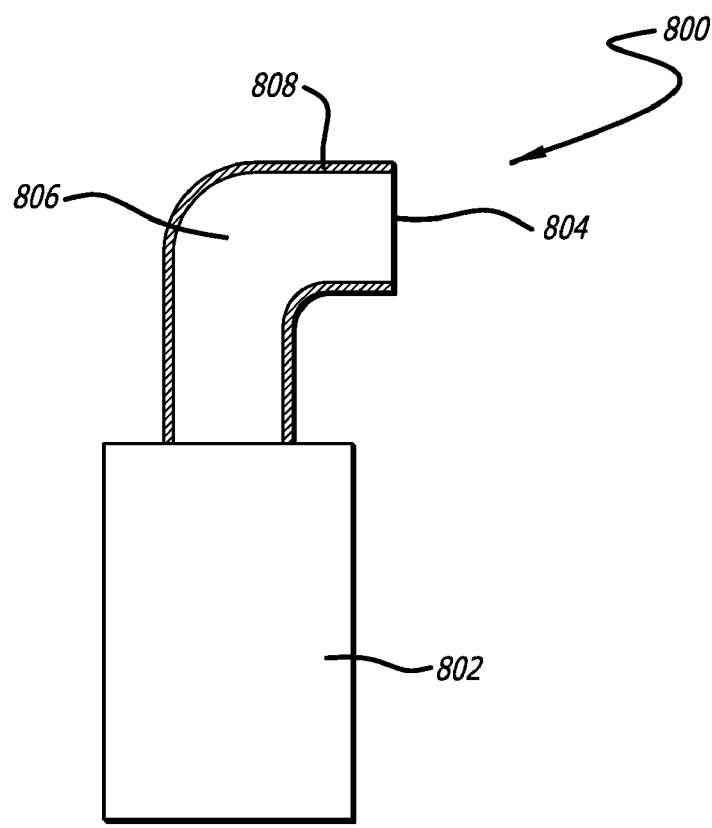
FIG. 8 illustrates an embodiment of a thimerosal removal device of the present invention in the form of an inhalation device.
Figure 8B:
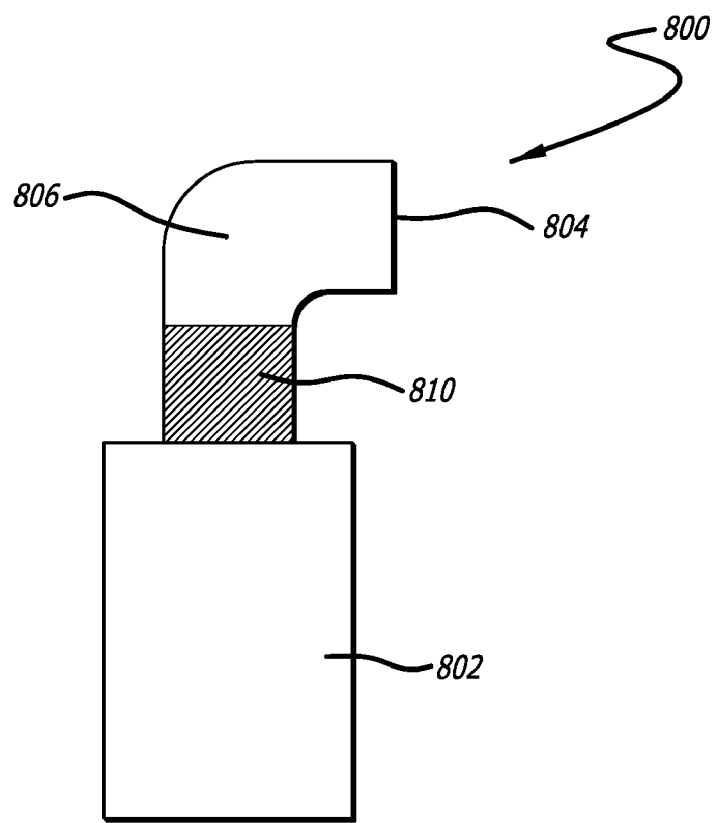

FIG. 8 graphically depicts an inhalation dosing device 800 comprises a body 802 in which is contained a medication to be administered to a patient by inhalation and an outlet 804. Suitable inhalation devices can deliver medications to the pulmonary system by inhaling through the nose or the mouth. The medication can be administered as an aerosol, a dry powder, or any form suitable for administration to the pulmonary system of a patient. Typically, the medication from the body 802 is propelled through a passageway 806 to an outlet 804 where it enters the nose or mouth of the patient. In one embodiment of the present invention presented in FIG. 8A, the interior of the passageway 806 and/or outlet 804 is coated with a polymer coating 808 to which at least one MT protein is bound. Inhalable medications containing thimerosal pass through passageway 806 and outlet 804 and thimerosal in the inhalable medication binds to the MT protein on polymer coating 808 such that a substantial amount of the thimerosal is removed from the inhalable medication prior to entering the patient. In another embodiment presented in FIG. 8B, a filter 810 having at least one MT protein bound thereto is disposed within passageway 806 such that inhalable medications containing thimerosal pass though filter 810 and thimerosal is removed from the inhalable medications prior to entering the patient. Inhalation dosing devices are well known in the art and exemplary devices are disclosed in U.S. Pat. Nos. 7,047,967, 7,143,764, 7,077,130, 7,032,594, 7,007,689, 6,955,169, 6,745,761, 6,557,550, 6,345,617, 6,131,566, 5,860,416, 5,571,246, 5,263,475, and 4,083,368, all of which are incorporated by reference for all they disclose regarding inhalation dosing devices.

Figure 9A:
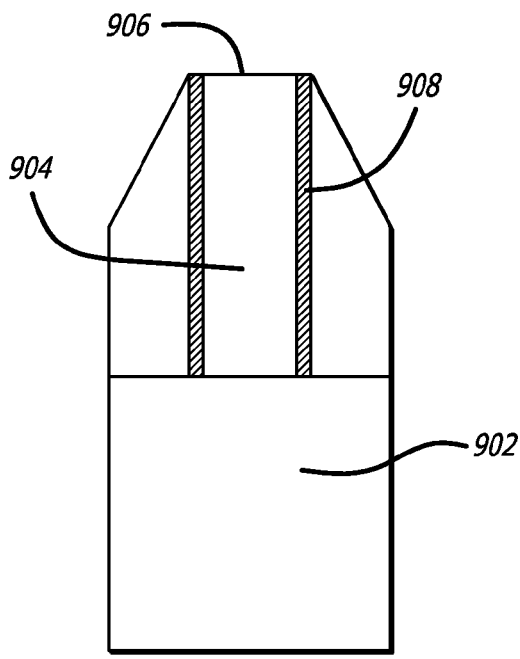
FIG. 9 illustrates an embodiment of a thimerosal removal device of the present invention in the form of an air gun injection device.
Figure 9B:
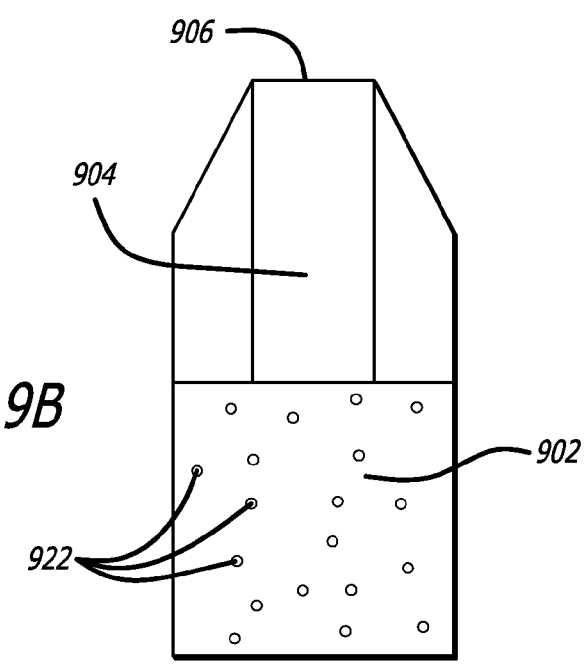
Figure 9C:
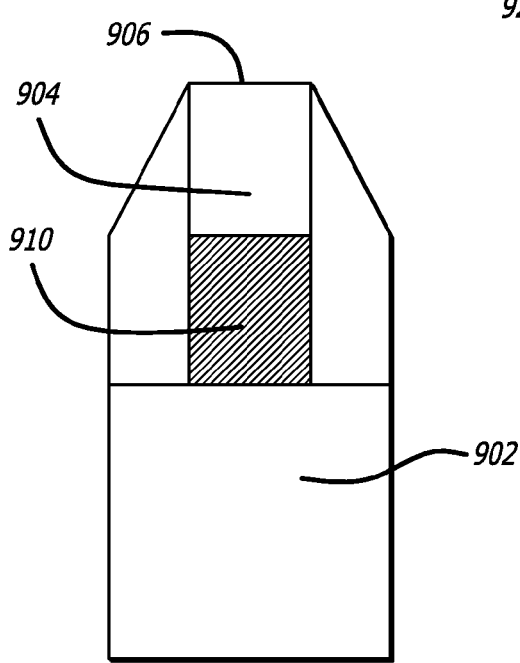

FIG. 9 depicts another exemplary dosing device, a needleless injection device. An exemplary needleless injection device 900 comprises a reservoir chamber 902 connected through a dispensing passageway 904 to an orifice 906 through which a medication is injected into a patient. Typically, the medication contents of chamber 902 are propelled through dispensing passageway 904 and orifice 906 with sufficient force such that the medication penetrates the skin of the patient. In one embodiment of the present invention depicted in FIG. 9A, the interior of the dispensing passageway 904 and/or outlet 906 are coated with a polymer coating 908 to which at least one MT protein is bound. Injectable medications containing thimerosal pass through dispensing passageway 904 and outlet 906 and thimerosal in the injectable medication binds to the MT protein on polymer coating 908 such that a substantial amount of the thimerosal present in the injectable medication is removed from the injectable medication prior to entering the patient. In another embodiment depicted in FIG. 9B, reservoir 902 contains beads 922 to which at least one MT protein is bound. Injectable medications containing thimerosal contact beads 922 in reservoir 902 such that a substantial amount of the thimerosal present in the injectable medication is bound to beads 922 prior to the injectable medication leaving the reservoir 902 and entering the patient. In another embodiment presented in FIG. 9C, a filter 910 having at least one MT protein bound thereto is disposed within dispensing passageway 904 such that injectable materials containing thimerosal pass though filter 910 and thimerosal is removed from the injectable medications prior to entering the patient. Needleless injection devices are well known in the art and exemplary devices are disclosed in U.S. Pat. Nos. 7,156,822, 7,150,409, 7,056,300, 7,029,457, 6,939,323, 6,471,669, 5,993,412, 5,520,639, 4,342,310, and 3,948,266, all of which are incorporated by reference for all they disclose regarding needleless injection devices.

In another embodiment of the present invention, the medication or bioactive material is mixed with a plurality of beads or nanoparticles having at least one MT protein bound thereto and the heavy metal-MT-bead complex is removed from the medication. Exemplary, non-limiting means for removal of heavy metal-bound beads from the mediation includes, but is not limited to, filters, membranes, meshes, affinity columns, and other means known to persons of ordinary skill in the art.

In yet another embodiment of the present invention, a filter unit, as depicted in FIG. 7B, is provided to remove thimerosal from a thimerosal-containing liquid. The filter housing 130 contains at least one MT protein bound to a solid support 136 enclosed with a housing having an inlet port 132 and an outlet port 134. The filter unit can be attached to commercially available syringe or other device to remove thimerosal from a thimerosal-containing liquid. The thimerosal is retained within the filter unit and a substantially thimerosal-free medication results from passage of the medication through the filter unit.

Polymeric coatings suitable for coating the interior of a dosing device should not be able to dissociate from the surface of the dosing device, be capable of irreversibly binding metallothionein and be able to be sterilized.

The MT proteins are associated with the support, such as a polymer membrane or bead, by covalent bonding of the MT protein to the support or incorporation of the MT proteins into the polymer matrix.

Figure 14:
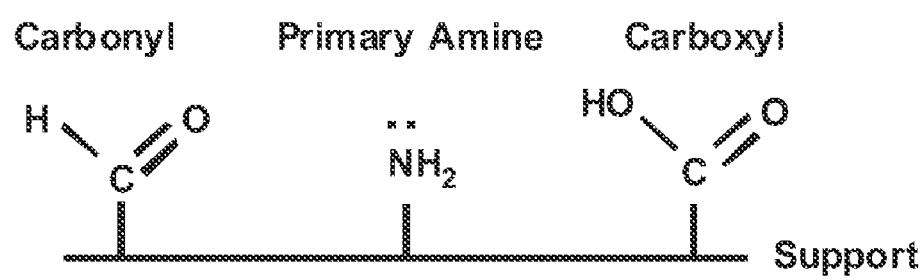
FIG. 14 depicts chemical groups derivatized on a solid support for immobilization of metallothionein according to the teachings of the present invention.

Many derivatized solid supports designed specifically for protein binding are commercially available and are well known to the skilled practitioner. Certain of these materials have surface aldehyde groups for linking proteins by way of a primary amine. In other cases, the support has been derivatized with either a primary amine or a carboxyl group (FIG. 14). For example, and not intended as a limitation, metallothionein can be i) linked directly to the material or ii) an appropriate linker can be used to orientate the MT away from the surface of the membrane to remove any potential protein/membrane steric interactions that would block the active site and prevent a ligand from binding to the MT. In the case of MT, the use of a linker may result in an increased efficiency of thimerosal binding.

The C-terminal amino acid of MT is a histidine. Since this residue is i) not part of the structural domains responsible for the metal binding activity and ii) is located away from the surface of the protein, it presents itself as an excellent site for coupling MT to a solid support. In one embodiment of the present invention, MT is coupled to a solid support by first reacting the support with N-succinimidyl iodoacetate (Formula 1).

Formula 1

Figure 15:
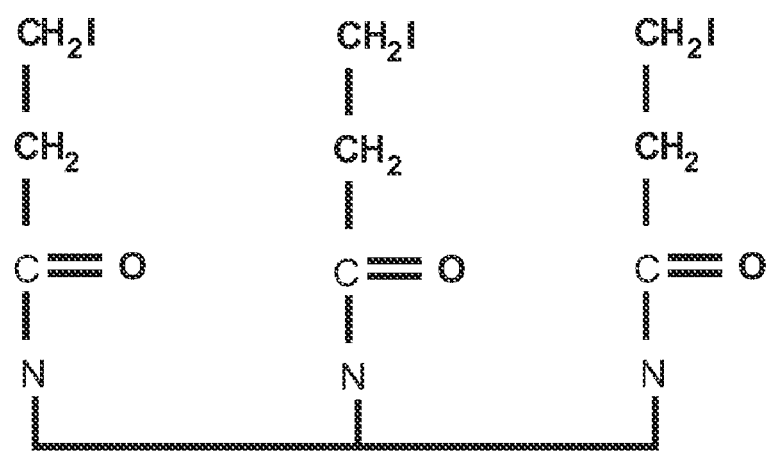
FIG. 15 depicts conversion of surface primary amines to iodoacetate functional groups a solid support for immobilization of metallothionein according to the teachings of the present invention.
Figure 16:
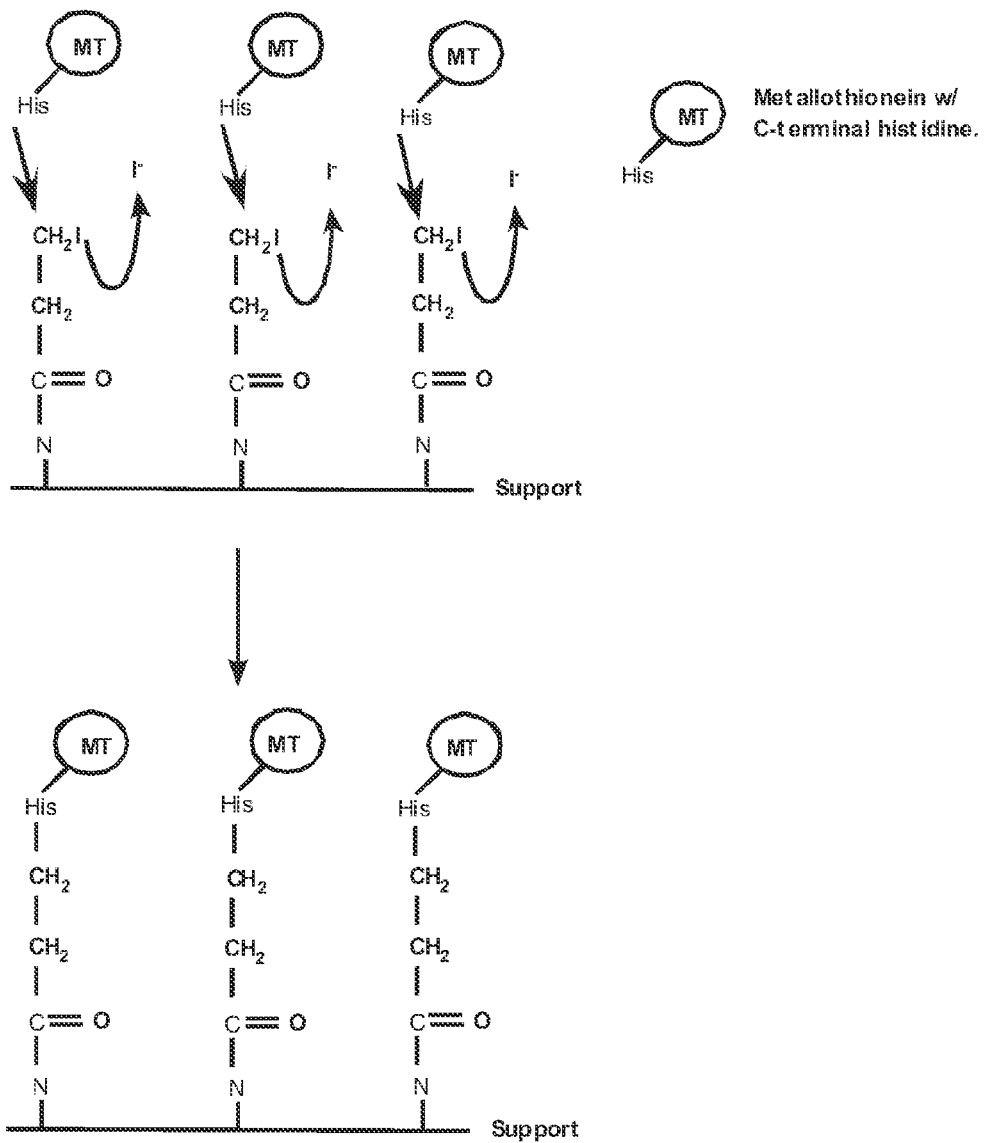
FIG. 16 depicts the covalent cross-linking of metallothionein to a solid support with surface iodoacetate functional groups according to the teachings of the present invention.

The N-hydroxysuccinamide (NHS) portion of the molecule reacts with the primary amines on the surface of the material to convert the surface functional groups to iodoacetate (FIG. 15). At a pH between 5 and 6, the iodoacetate functional groups react with the MT histidine, covalently linking the protein to the membrane (FIG. 16).

Figure 17:
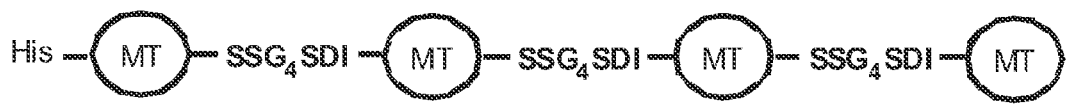
FIG. 17 depicts a metal binding molecule comprising multiple copies of metallothionein linked through a nonapeptide according to the teachings of the present invention.

Additionally, increasing the number of MT molecules on the membrane can increase the total thimerosal binding capacity of the membrane. Since the membrane has a defined surface area with a finite number of functional groups (iodoacetate) available for linking protein to the membrane, another method will be required to increase the number of MT molecules on the membrane. This can be accomplished by cloning multiple copies of the *Artemia* MT gene within a standard cloning vector to form a polymeric MT gene sequence. In one embodiment of the present invention, the final expressed MT "protein" would be composed of multiple copies of MT separated by a linker such as, but not limited to, a nonapeptide ($SSG_4SDI$, SEQ ID NO. 24) linker (FIG. 17).

The linker sequence is designed to i) allow the MT sequences to fold into their native conformation and retain their thimerosal binding activity and ii) impart a degree of rigidity that prevents the individual MT protein domains from aggregating. Using the exemplary MT sequence depicted in FIG. 16, the thimerosal binding capacity would increase four-fold.

The polymeric MT gene sequence would be constructed using overlapping PCR primers standard recombinant DNA technology. The construct can then be PCR amplified with primers containing unique restriction sites i) not present in the construct and ii) compatible with the multiple cloning site of a suitable expression vector. The resulting PCR product is then cloned into the expression vector such as, but not limited to, the pET expression vector. The recombinant plasmid is then used to transform suitable expression cells such as, but not limited to, BL2(D3) cells. If the expression vector contains an inducible promoter, protein expression is induced by the addition of a molecule such as, but not limited to, IPTG. The resultant protein is then purified as described below for monomeric MT.

The expressed MT proteins are purified using standard techniques. Techniques for purification of cloned proteins are well known in the art and need not be detailed further here. One particularly suitable method of purification is affinity chromatography employing an immobilized antibody to a metal binding protein. Other protein purification methods include chromatography on ion-exchange resins, gel electrophoresis, isoelectric focusing, and gel filtration, among others. Alternatively, the MT proteins of the present invention can be purified following their expression from modified organisms by methods such as precipitation with reagents (e.g. ammonium sulfate, acetone or protamine sulfate as well as other methods known in the art).

The MT proteins of the present invention can be isolated easily and efficiently from natural sources or synthetically produced. In one embodiment of the present invention, the MT proteins are isolated from brine shrimp (*Artemia*). *Artemia* MT comprise a family of metal binding proteins that are referred to as "isomers". Analysis of these proteins' unique amino acid compositions showed each isoform to be essentially equivalent. At least five individual *Artemia* MT isoforms have been identified. Unlike MTs from other organisms which share a high degree of sequence homology or similarity, the *Artemia* metal binding proteins have unexpectedly different structural characteristics but possess a high degree of sequence homology to one another.

Amino acid sequence analysis indicated that the metal binding motif of the first six cysteine residues of the *Artemia* metal binding protein was conserved when compared to rabbit and human MTs, indicating the importance of these amino acid residues in the protein's metal binding function (Hamer D H, Metallothionein. Ann. Rev. Biochem. 55:813-51, 1986). This conservation of the cysteine-rich metal binding motif is seen across a wide variety of divergent species (FIG. 6).

Figure 1:
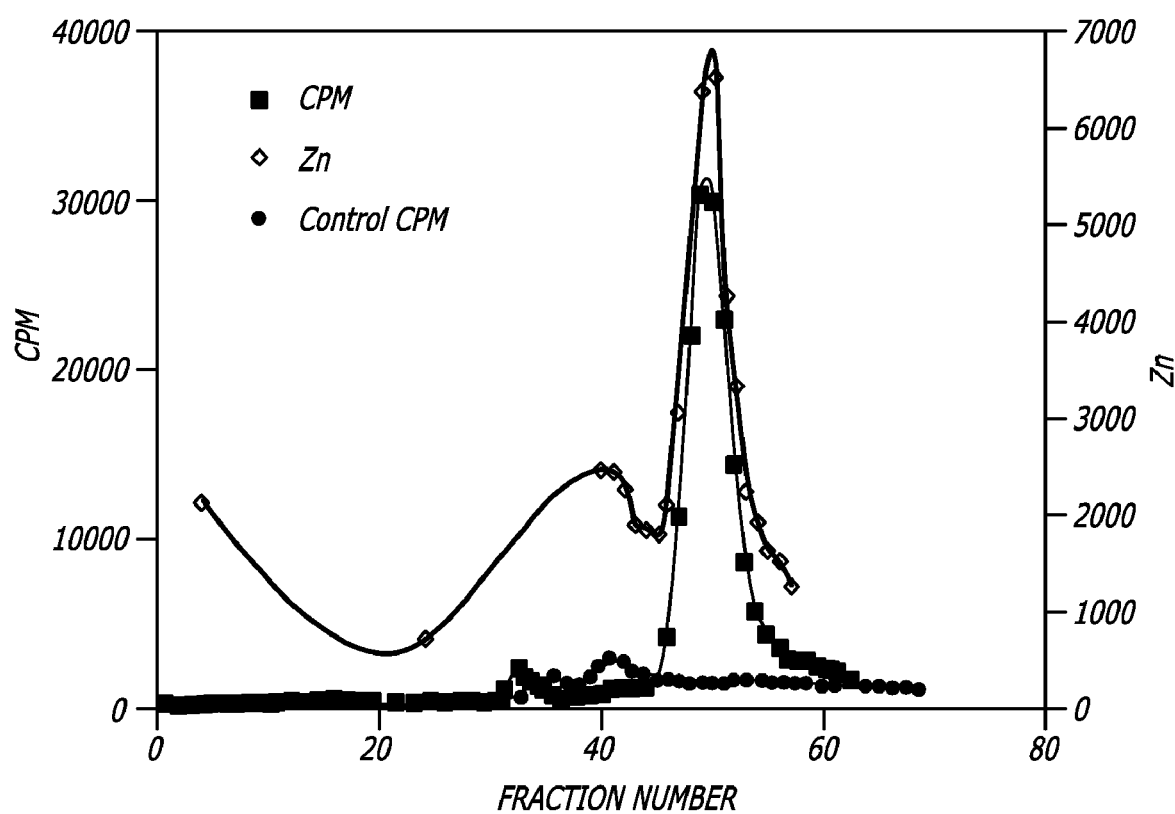
FIG. 1 is an elution profile of exemplary metal binding proteins of the present invention illustrating co-elution of metal binding proteins with the heavy metal zinc.

FIG. 1 details an exemplary elution profile utilizing an exemplary MT protein of the present invention. This profile was obtained utilizing the following exemplary protocol. *E. coli* (Strain ER 2566) were transformed with a plasmid expression vector containing the MT gene sequence of SEQ ID NO. 1 in pTMZ. Bacteria were grown in LB broth containing 1% glucose at 37° C. to an $A_{600}$ of 0.60. The bacterial cells were collected and resuspended in LB broth containing 0.1% glucose and incubated for 45 minutes at the same temperature. Isopropyl β-D-thiogalactopyranoside (IPTG) was added to a final concentration of 0.1 mM. The bacterial cells were incubated for about 16 hours. Non-transformed bacteria were used as controls. The cells were collected by centrifugation and sonicated in 10 mM Tris, pH 8.0, 5 mM dithiothreitol (DTT) and 0.5 mM phenylmethylsulfonylfluoride (PMSF). The homogenate was centrifuged at 150,000×g for 1 hour at 4° C. The supernatant was collected and incubated with 2 µCi of $^{109}$Cd at room temperature. The radiolabeled supernatant was then applied to a G-50 molecular exclusion column and eluted with 50 mM Tris, pH 8.0. Five milliliter fractions were collected and assayed for radioactivity (CPM) and zinc (Zn), the zinc being an endogenous metal that associates with the exogenous metal binding protein expressed by the transformed bacteria. Each fraction eluting from the column was assayed for Zn by ICPMS (Inductively Coupled Plasma Mass Spectroscopy). Other nucleotide sequence that encode a functional metal binding protein, including, but not limited to SEQ ID NO. 3, may also be utilized, as provided and disclosed by the teachings of the present invention.

A substantially purified MT protein in accordance with the teachings of the present invention has an amino acid sequence analogous to:

an amino acid having similar structural or chemical properties. Those skilled in the art can determine which amino acid residues may be substituted, inserted or altered without the metal binding properties of the proteins of the present invention.

Other substitutions can also be considered conservative, depending upon the environment of the particular amino acid. For example, glycine and alanine can be interchangeable, as can be alanine and valine. Methionine, which is relatively hydrophobic, can be interchanged frequently with leucine and isoleucine, and sometimes with valine. Lysine and arginine are interchangeable in locations in which the significant feature of the amino acid residue is its charge and the different pKs of these two amino acid residues and where their different sizes are not significant. Still other changes can be considered "conservative" in particular environments, as known in the art.

For example, if an amino acid on the surface of a protein is not involved in a hydrogen bond or salt bridge interaction with another molecule, such as another protein subunit or a ligand bound by the protein, negatively charged amino acids such as glutamic acid and aspartic acid can be substituted with positively charged amino acids such as lysine or arginine and vice versa. Histidine, which is more weakly basic than arginine or lysine, and is partially charged at neutral pH, can sometimes be substituted for these more basic amino acids as well. Additionally, the amides glutamine and asparagine can sometimes be substituted for their carboxylic acid homologues, glutamic acid and aspartic acid.

For example, these MT proteins are capable of heavy metal binding under a range of temperature conditions such as, for example, a temperature range of about 4° C. to about 100° C. and therefore particularly ideal for many applications. Those skilled in the art will appreciate that depending on a particular application or operation in which the MT proteins are to be utilized, a particular temperature range may be preferred for practical or economic reasons.

```
                                                SEQ ID NO. 2
MET ASP CYS CYS LYS ASN GLY CYS THR CYS ALA PRO ASN CYS LYS   15

CYS ALA LYS ASP CYS LYS CYS CYS LYS GLY CYS GLU CYS LYS SER   30

ASN PRO GLU CYS LYS CYS GLU LYS ASN CYS SER CYS ASN SER CYS   45

GLY CYS HIS                                                   48
```

Also within the scope of the present invention are substantially purified MT proteins that are variants of the sequence of the above SEQ ID NO. 2 that preserve the protein's metal binding affinity. In particular, conservative amino acid substitutions within the scope of the present can include any of the following: (1) any substitution of isoleucine for leucine or valine, leucine for isoleucine, and valine for leucine or isoleucine; (2) any substitution of aspartic acid for glutamic acid and of glutamic acid for aspartic acid; (3) any substitution of glutamine for asparagine and of asparagine for glutamine; and (4) any substitution of serine for threonine and of threonine for serine.

A "conservative amino acid substitution" as used herein, refers to alteration of an amino acid sequence by substituting Turning now to an exemplary discussion of the genetic engineering of the novel metal binding proteins of the present invention, a nucleotide sequence for one of the isoforms of an MT protein from a brine shrimp (*Artemia*) was identified, as discussed above. Generally, the isolation process comprises: (1) preparation of one or more sample(s) containing nucleic acids from brine shrimp (*Artemia*); (2) isolation of total RNA from *Artemia*; (3) preparation of cDNA from the total RNA; (4) amplification of metal binding protein gene sequences; and (5) cloning, sequencing and verification of an isolated nucleic acid sequence as an MT protein gene from *Artemia*.

The above procedure yielded the entire coding sequence for *Artemia* MT. This sequence is:

```
                                                              SEQ ID NO. 1
5'-ATG GAC TGC TGC AAG AAC GGT TGC ACC TGT GCC CCA AAT TGC AAA    45

TGT GCC AAA GAC TGC AAA TGC TGC AAA GGT TGT GAG TGC AAA AGC    90

AAC CCA GAA TGC AAA TGT GAG AAG AAC TGT TCA TGC AAC TCA TGT   135

GGT TGT CAC TGA-3'                                            147
```

Species as divergent as humans and wheat express metallothionein proteins with similar binding affinities for heavy metals. These MT proteins contain from 12 to 22 cysteine residues, which are conserved across divergent species. These cysteine residues form metal binding motifs responsible for the metal binding function of the proteins (Hamer D H, Metallothionein. Ann. Rev. Biochem. 55:813-51, 1986). Therefore, one embodiment of the present invention provides MT proteins immobilized on solid supports, such as membranes, wherein the MT are isolated from organisms including, but not limited to, mammals, plants, fish, mollusks, echinoderms, crustaceans, reptiles, nematodes, grains, bacteria, algae, yeast and fungi. Non-limiting examples of these organisms include, but are not limited to, brine shrimp (*Artemia*), rabbit (*Oryctolagus cuniculus*), green monkey (*Cercopithecus aethiops*), human (*Homo sapiens*), channel catfish (*Ictalurus punctatus*), African clawed frog (*Xenopus laevis*), blue mussel (*Mytilus edulis*), painted sea urchin (*Lytechinus pictus*), fruit fly (*Drosophila melanogaster*), roundworm (*Caenorhabditis elegans*), rice (*Oryza sativa*), wheat (*Triticum aestivum*) and yeast (*Candida glabrata*).

One embodiment of the present invention provides one or more nucleic acid sequences encoding a substantially purified MT protein having amino acid sequence analogous to at least one metallothionein protein from an organism including, but not limited to, *Artemia*, mammals and marine species, or other species having a metallothionein protein with conserved amino acid sequence homology in the cysteine residues, e.g. the metal binding motifs, as compared to *Artemia* MT (FIG. 6).

Another embodiment of the present invention provides one or more amino acid sequences encoding a substantially purified MT protein analogous to at least one metallothionein protein from an organism including, but not limited to, *Artemia*, mammals and marine species, or other species having a metallothionein protein with conserved amino acid sequence homology in the cysteine residues, e.g. the metal binding motifs, as compared to *Artemia* MT (FIG. 6). Exemplary amino acid sequences include the sequences of SEQ ID NO. 2 and SEQ ID NOs. 11-23 (FIG. 6).

Alternatively, an isolated nucleic acid can comprise the minimal DNA sequences sufficient to allow translation of a functional MT protein. A functional MT protein need not be the entire native MT protein but can be just those portions or regions that encode a protein, or a synthetic chemical complex, capable of binding to heavy metals, in a non-limiting example the sequence of SEQ. ID. NO. 3. Therefore, the invention also includes isolated nucleic acids including DNA having at least 80% sequence identity to a DNA molecule having the sequence of nucleotide residues 1 to 66 of SEQ ID NO. 1.

Also within the present invention is a nucleic acid sequence encoding any one of the MT proteins. Such MT proteins can have molecular weight of about 5,800 daltons and are able to bind with high affinity to heavy metal ions such as arsenic, zinc, copper, cadmium, mercury, cobalt, lead, nickel, platinum, gold, silver and complexes thereof. The MT proteins include therein an amino acid sequence selected from the group consisting of SEQ ID NO: 2, SEQ. ID. NOs. 11-23 and sequences incorporating one or more conservative amino acid substitutions thereof wherein the conservative amino acid substitutions are any of the following: (1) any of isoleucine, leucine and valine for any other of these amino acids; (2) aspartic acid for glutamic acid and vice versa; (3) glutamine for asparagine and vice versa; and (4) serine for threonine and vice versa. Alternative nucleic acid sequences can be determined using the standard genetic code; the alternative codons are readily determinable for each amino acid in this sequence. Additionally, it is within the scope of the present invention to make additional mutations, deletions or additions to the amino acid or nucleic acid sequences of the MT proteins disclosed herein which do not effect the metal binding capabilities of the resultant MT protein.

The MT proteins used in these metal binding processes can be provided as a product purified from its natural source or can be produced by bioengineering techniques. For example, the MT proteins can be produced by transgenic or modified organisms. Modified organisms include, but are not limited to, transgenic animals, bacteria, plants, yeast, mammalian cells, insect cells and algae.

Methods for reducing the concentration of heavy metals in a substrate include contacting an MT protein with a substrate having heavy metals. In a non-limiting example, an MT protein having an amino acid sequence analogous to at least one metal binding protein sequence from brine shrimp (*Artemia*) can be contacted with a substance having a concentration of at least one heavy metal to bind the heavy metal to the MT protein. Subsequently, the bound heavy metal can be separated from the substrate, reducing the concentration of heavy metals in the original substrate.

Methods for reducing the concentration of heavy metals in a substance include producing the metal binding proteins in a modified organism. Modified organisms include, for example, transgenic organisms or transgenic hosts. For example, hosts or organisms such as shrimp, plants, bacteria, yeast or algae can be modified using molecular and genetic engineering techniques well known in the art. Using these techniques, which are described for example, in Sambrook et al., Molecular Cloning: A Laboratory Manual (New York: Cold Spring Harbor Press, 2001); Ausubel et al. Current Protocols in Molecular Biology (Wiley Interscience Publishers, 1995); US Dept Commerce/NOAA/NMFS/NWFSC Molecular Biology Protocols; or Protocols Online, organisms whose genomes are modified so as to result in expression of an MT protein are provided.

A modified organism producing an MT protein includes a modified organism producing at least one MT protein having an amino acid sequence substantially similar to a metal binding protein from a brine shrimp (*Artemia*). A modified organism also includes an organism producing an MT protein having an amino acid sequence substantially similar to SEQ ID NO. 2 or conservative amino acid substitutions thereof.

Alternatively, production or expression of the MT proteins from modified organisms is not limited to genomic expression of the metal binding proteins, but also includes epigenetic expression from the modified organisms. Methods and techniques for obtaining epigenetic expression from a modified organism include, for example, adenoviral, adeno-associated viral, plasmid and transient expression techniques which are known in the art.

Methods for producing the MT proteins of the present invention are also disclosed herein. For example, a method for producing an MT protein having an amino acid sequence analogous to at least one MT protein from a brine shrimp (*Artemia*) includes providing an expression system, producing an MT protein using the expression system and purifying or isolating the MT proteins.

Expression systems can be systems such as traditional manufacturing plants. For example, organisms such as brine shrimp can be grown and the MT proteins purified or extracted from the tissues of the brine shrimp. Alternatively, biomanufacturing systems using genetically engineered organisms (produced as described herein) capable of producing the MT proteins can be used. For example, bacteria containing an MT protein expression vector can be cultured on large or small scale (depending on the particular need). The MT proteins can then be purified from the bacterial broth and used to remove heavy metals from a variety of substrates.

Therefore, an MT protein can be produced by expression of a nucleic acid sequence encoding an MT protein in a modified organism or host cell. Such a nucleic acid sequence includes, for example, a MT gene such as SEQ ID NO. 1 or a sequence encoding a fragment or functional metal binding domain of a MT gene.

A further understanding of the present invention will be accorded to those skilled in the art from a consideration of the following non-limiting Examples. It is emphasized that these Examples are illustrative of the principles and teachings of the present invention and are not intended to limit the scope of the invention.

EXAMPLE 1

Isolation of MT from *Artemia*

In accordance with the teachings of the present invention, the following exemplary protocols illustrate methods useful in the production, purification and analysis of MT proteins.

Sample Preparation

As a preliminary step in the isolation of the metal binding proteins, *Artemia* brine shrimp were grown in artificial seawater (AS) (422.7 mM NaCl, 7.24 mM KCL, 22.58 mM $MgCl_2.6H_2O$, 25.52 mM $MgSO_4.7H_2O$, 1.33 mM $CaCl_2.2H_2O$ and 0.476 mM $NaHCO_3$). *Artemia* cysts (2.5 g) were incubated for 48 hours in 250 mL of AS supplemented with antibiotics at 30° C. and rotation at 125 rpm. After 24 hrs, phototropic *Artemia* were collected, cultured for an additional 24 hrs and then collected by cloth filtration. The shrimp were weighed and if not used immediately, stored at −80° C.

The *Artemia* were then homogenized in homogenization buffer (HB) (10 mM Tris-HCl (pH 8.0), 0.1 mM DTT, 0.5 mM PMSF and 10 µg/ml Soybean Trypsin Inhibitor) and resuspended in HB at 4 mL/gm wet weight of shrimp. The homogenate was passed through a Yamato LH-21 homogenizer three times at a setting of 800 rpm, filtered through Miracloth (Calbiochem) and the filtrate centrifuged in a Sorvall SA-600 rotor at 14,300 rpm, 4° C. for 30 min. The lipid layer on top of the supernatant was removed by vacuum aspiration and the lower supernatant layer collected and centrifuged in a Beckman 50.2TI rotor at 40K rpm, 4° C. for 90 min. Again, the upper lipid layer was removed and the lower supernatant recentrifuged at 150,000×g (150K sup). The 150K sup was then used immediately or stored at −80° C. If used immediately, this product was then subjected to gel filtration as follows. The gel filtration studies verified the metal binding proteins' ability to bind to heavy metals.

Gel Filtration Studies

The 150K sup was filtered through a HPLC certified 0.45 micron LC13 acrodisc filter (Gelman Sciences). A 20 mL aliquot of filtered 150K supernatant was incubated at 4° C. for 20 min with 2 µL of $^{109}Cd$ (0.066 µCi) to radiolabel the metal binding proteins. The sample was then applied to a Sephadex G-50 molecular weight exclusion column (2.6 cm×94 cm) previously equilibrated with 50 mM Tris-HCl (pH 8.0) saturated with $N_2$. One molar DTT (2 µL) was added to fractions 60-100 prior to sample loading in order to maintain reducing conditions in the fractions containing the low molecular weight metal binding proteins. The column was eluted with 50 mM Tris (pH 8.0) at a flow rate of 20 mL/hr while monitoring the eluate at 280 nm. During the elution period, the buffer reservoir was continually purged with $N_2$. Samples used for amino acid analysis were not radiolabeled.

The $^{109}Cd$ content (CPM) of the column fractions was determined with an Auto-Logic gamma counter (ABBOTT Laboratories). Zinc content was measured by Flame or Furnace Atomic Absorption Spectroscopy and expressed as PPB zinc/fraction. Prior studies indicated that two classes of metal binding proteins were present, one class being a high molecular weight fraction. However, the majority of $^{109}Cd$ eluted with a low molecular weight class of zinc-containing metal binding protein. As shown in FIG. 1, radioactive metal binding protein had a elution peak corresponding to that for zinc (roughly, fraction #50) indicating the presence of endogenously bound zinc. The protein concentration of the Sephadex G-50 fractions was determined with a BCA Total protein assay kit (Pierce) according to manufacturers protocol. The distinct structural features of the metal binding proteins of the present invention were then identified in the following studies.

Metal Binding Protein Characterization Studies

Chromatographic and molecular weight studies were performed to ascertain structural features of the metal binding proteins. All protocols used were as described previously in B. Harpham, "Isolation of Metal Binding Proteins From *Artemia*", Master's Thesis, California State University, Long Beach Library, 1998. Using anion exchange and reverse phase chromatography techniques well known in the art and described, for example, in B. Harpham "Isolation of Metal Binding Proteins From *Artemia*", supra, metal binding proteins from *Artemia* were purified and determined to have molecular weights and amino acid sequence length unexpectedly lower than other known metal binding proteins. Under SDS-PAGE conditions, *Artemia* metal binding proteins have molecular weight of about 5.8 kDa as compared to 6-7 kDa for metal binding proteins from other mammalian species. Protein analysis of *Artemia* metal binding proteins indicate a sequence length of 48 amino acids. The *Artemia* MT amino acid sequence was unexpectedly and significantly shorter in length than other known metal binding proteins, which range in length from 60 to 68 amino acid residues.

EXAMPLE 2

Cloning and Sequencing of a Gene Encoding Artemia Metal Binding Protein

Total RNA was isolated from 48 hour nauplii (the larval stage of *Artemia*) using the RNAzol method. Forty-eight hour nauplii samples were prepared as described above in Example 1. The PolyTract Procedure (Promega, Wis.) was then used to isolate mRNA from the total RNA samples. cDNA was generated from the mRNA using SuperScript and 3' RACE Kit procedures (Cat #18373, Gibco/BRL, WI) and then subjected to the following synthesis reaction.

cDNA synthesis reaction:
*Artemia* mRNA 25 µl (500 ng)
DEPC $H_2O$ 30 µl
10 µM AP 5 µl The above mixture was incubated for 10 min at 70° C., then placed on ice for 1-2 min. Volatilized liquid was collected by centrifugation for 10 sec at 10,000 rpm. The following were then added to the above RNA cocktail to produce a cDNA solution:

10×PCR Buffer 10 µl
25 mM $MgCl_2$ 10 µl
10 mM dNTP 5 µl
0.1 mM DTT 10 µl

The above resulting cDNA solution was then mixed and incubated at 42° C. for 5 min. Five (5) µL of Superscript II RT was added and the mixture incubated at 42° C. for 50 min for cDNA synthesis. The reverse transcription reaction was terminated by incubating the solution for 15 min at 70° C.; 5 µL of RNase was then added and the solution incubated for 20 min at 37° C. The final solution containing *Artemia* cDNA was then stored at −20° C. until used for PCR amplification as described below.

The initial PCR Primer Sequences used were as follows: the 5' primer (N-terminal side) was designated "MT-Not I" (SEQ ID NO. 5) and the 3' primer (C-terminal side) was designated "dT-Spe I" (SEQ ID NO. 6, SEQ ID NO. 7, SEQ ID NO. 8, or SEQ ID NO. 9)

```
                                           SEQ ID NO.5
5'-ACC TAT GCG GCC GCA AAT GGA CTG CTG CAA GAA C-
3'

SEQ ID NO.6
5'-GCA CCA ACT AGT GCC TTT TTT TTT TTT A-3'

SEQ ID NO.7
5'-GCA CCA ACT AGT GCC TTT TTT TTT TTT C-3'

SEQ ID NO.8
5'-GCA CCA ACT AGT GCC TTT TTT TTT TTT G-3'.
```

The above 5' and 3' primers were then used in the following amplification cocktail.

PCR Reaction Cocktail:
10×PCR Buffer 5 µl
25 mM $MgCl_2$ 3 µl
10 mM dNTP 1 µl
10 µM dT-SpeI 1 µl
10 µM MT-Not I 1 µl To the above PCR Reaction Cocktail, a Gem 50 wax bead was added to the tube and the tube incubated at 80° C. for 2-3 minutes. Upon hardening of the wax at room temperature for 10-15 min, the following were layered on top of the hardened wax:

Sterile $H_2O$ 36.5 µl
*Artemia* cDNA mixture 2 µl
Taq Polymerase 0.5 µl

This final mixture was then subjected to the following PCR amplification program.

PCR Program:
Initial denaturation for 3 min at 95° C., followed by 29 cycles of:
94° C. for 1 min
49° C. for 1 min
72° C. for 1 min
Then one cycle of:
72° C. for 10 min
Then holding the mixture at 4° C.

Once amplified, the PCR product was verified for successful amplification on a 1.2% agarose gel. The PCR product was then purified for subsequent cloning using Qiagen QIAquick Gel Extraction (Qiagen, Calif.). The following primers which contain modifying restriction sites incorporated into their sequence were used to amplify and subclone the purified PCR product containing brine shrimp *Artemia* metal binding protein gene sequences.

MT Nco I (5' primer containing an Nde I site):

```
                                           SEQ ID NO.9
5'-GCT ACA CAT ATG TCC ATG GAC TGC TGC AAG AAC-3'
```

MT Sal I (3' primer containing Sal I site):

```
                                           SEQ ID NO.10
5'-ACG AAC GTC GAC GCC TTT TTT TTT TTT A-3'
```

Using the MT Nco I and MT Sal I primers, with an annealing temperature of 72° C. for 1 min, the *Artemia* MT nucleotide sequence was amplified and then subsequently cloned into TOPO CR2.1 using TA cloning and then subcloned into the pGEM3 vector's Eco R1 site. Once cloned, the cloned metal binding protein gene can then be easily modified or further processed for use in expression, production or other methods requiring use of an isolated nucleic acid sequence encoding a metal binding protein.

The entire coding sequence for MT gene was then determined using a Applied Biosystems DNA sequencer. Sequence comparison studies of the MT gene from *Artemia* indicate it to have unexpectedly different sequence as compared to other known metal binding protein genes. When the *Artemia* MT gene sequence was aligned with that of equine and human MT, homology was observed at the locations of the metal-binding cysteine residues. The ability of the exemplary metal binding protein of the present invention to bind heavy metals was then confirmed in the following studies.

EXAMPLE 3

Polymer Membranes for Toxic Metal Removal from Water

Metallothionein was extracted from *Artemia* embryos as described above. The protein extract (80 mL) was placed in a boiling water bath for 15 minutes. The solution was centrifuged at 30,000×g (16,000 rpm in a SA600 rotor) for 30 minutes at 4° C. The supernatant containing the metallothionein was transferred to a clean tube containing 60 μL of $^{109}$Cd (Amersham Biosciences). The solution was mixed well and allowed to stand at room temperature for five minutes. This allows for exchange of the radioactive cadmium onto the metallothionein and provides us with a method for detecting the protein during its purification. The solution was then applied to a 100×4.8 cm G-50 molecular exclusion column and eluted with nitrogen saturated 50 mM Tris, pH 8.0. Fifteen milliliter fractions were collected into tubes containing 25 μL of 1M DTT. The fractions with peak metal binding activity were pooled and stored at 4° C. The solution is referred to as MT. (See FIG. 1)

Metal Binding at Neutral pH

Pall Biodyne membranes (Biodyne A and Biodyne B, 0.45 μm, Lot numbers 002245 and 035241, respectively) were used as a solid support for these experiments. A 1 cm$^2$ piece of membrane was placed in a 10 mL Millipore glass frit filtering unit. Ten milliliters of MT was passed through the membrane under vacuum at a flow rate of approximately 100 mL/minute (FIG. 3). The flow through was collected for protein analysis. Next, 10 mL of a solution of cadmium (0.1 μg/mL of $CdCl_2$ and 10 μL $^{109}$Cd in 50 mL of water) was passed through the membrane under vacuum (FIG. 4). The membrane was then washed twice, each with 10 mL of PBS. Five milliliters of the pooled eluate was analyzed for radioactivity. The membrane was removed from the filtering unit, place in a 12×75 mm centrifuge tube and analyzed for radioactivity in an LKB gamma counter. As a control, the procedure was repeated with a second membrane that had not been treated with MT. This membrane is referred to as the "blank." The results are shown below in Table 1.

TABLE 1

| Sample | MT Membrane | Blank |
|---|---|---|
| Biodyne A | 152,876 | 3768 |
| Biodyne B | 158,762 | 1774 |

The results demonstrate that membrane-bound MT is capable of removing cadmium (as $^{109}$Cd) from a solution of the metal passed through the membrane. Membranes without MT remove little, if any, metal from the solution.

Metal Binding at Varying pH

The next series of experiments were to determine the effect of extremes of pH on the metal binding activity of the protein on the membrane. A fresh sample of MT was prepared for these studies. The solution of cadmium used for these experiments was prepared as follows: 2 μL of $^{109}$Cd was added to 1 mL of an aqueous solution of $CdCl_2$ (1 ppm). Then 100 μL of this radioactive cadmium solution was added to 10 mL of each of the following solution: PBS, 10 mM glycine, 150 mM NaCl, pH 3.0, and 10 mM $H_2CO_3/HCO_3$, 150 mM NaCl, pH 10.1. Only the Biodyne A membrane was used for this study. Membranes not treated with MT and washed with PBS containing radioactive cadmium served as the control. Membranes were placed in the Millipore filtering unit and processed as follows:

Membrane #1 (blank) was washed with 5 mL of PBS containing radioactive cadmium. The membrane was then washed twice with 10 mL of non-radioactive, metal-free PBS.

Membrane #2 was washed first with 10 mL of MT solution and then 5 mL of PBS containing radioactive cadmium. The membrane was then washed twice with 10 mL of non-radioactive, metal-free PBS.

Membrane #3 was washed with 10 mL of MT solution and then 5 mL of 10 mM $H_2CO_3/HCO_3$, 150 mM NaCl, pH 10.1, containing radioactive cadmium. The membrane was then washed twice with 10 mL of non-radioactive, metal-free 10 mM $H_2CO_3/HCO_3$, 150 mM NaCl, pH 10.1.

Membrane #4 was washed with 10 mL of MT solution and then 5 mL of 10 mM glycine, 150 mM NaCl, pH 2.0, containing radioactive cadmium. The membrane was then washed twice with 10 mL of non-radioactive, metal-free 10 mM glycine, 150 mM NaCl, pH 2.0.

Each membrane was analyzed for radioactivity as described above, The results are shown below in Table 2.

TABLE 2

| Sample | CPM |
|---|---|
| Membrane 1 (blank) | 174 |
| Membrane 2 pH 7.5 | 33380 |
| Membrane 3 pH 10.1 | 6890 |
| Membrane 4 pH 2.0 | 651 |

This experiment demonstrates that the membrane-bound MT is capable of binding metal at pHs ranging from 7.5 to 10.1 but not at a pH of 2. Once metal is bound to the MT, it can be recovered by exposing the membrane to acid (pH=2). These experiments were conducted by adding all the solutions directly to the membrane. To evaluate effects of pre-equilibrating the membranes with buffer prior to addition of MT, i.e., is the efficiency of metal binding effected, membranes (Biodyne B) were processed as follows:

Membrane #1 (blank) was washed with 5 mL of PBS containing radioactive cadmium. The membrane was then washed twice with 10 mL of non-radioactive, metal-free PBS.

Membrane #2 was washed first with 10 mL of MT solution and then 5 mL of PBS containing radioactive cadmium. The membrane was then washed twice with 10 mL of non-radioactive, metal-free PBS.

Membrane #3 was pre-washed with 10 mL of metal-free 10 mM $H_2CO_3/HCO_3$, 150 mM NaCl, pH 10.1, then washed with 10 mL of MT solution and then 5 mL of 10 mM $H_2CO_3/HCO_3$, 150 mM NaCl, pH 10.1, containing radioactive cadmium. Finally, the membrane was washed twice with 10 mL of non-radioactive, metal-free 10 mM $H_2CO_3/HCO_3$, 150 mM NaCl, pH 10.1.

The results are shown below in Table 3.

TABLE 3

| Sample | CPM |
|---|---|
| Membrane #1 | 190 |
| Membrane #2 | 4218 |
| Membrane #3 | 7431 |

Equilibrating the membrane at pH 10.1 results in better efficiency of protein binding to the membrane.

Specificity of MT Metal Binding

Binding affinity/specificity was measured against bovine serum albumin, a protein containing several cysteine residues and known to bind heavy metals. The Biodyne A membrane was used for this experiment. The concentration of MT solution was found to be approximately 7 μg/mL. The concentration of the flow through is equivalent to the starting material indicating that the amount bound to the membrane is in ng (nanograms), thus indicating that the metal binding capacity of the protein is significant. Therefore, 7 µg/mL and 100 µg/mL solutions of BSA were made in D-PBS using the 2 mg/mL BSA standard from Pierce Chemical, Inc. The cadmium binding solution was prepared as follows: 1.5 mL of aqueous 1 ppm $CdCl_2$ was mixed with 3 µL of $^{109}Cd$. The solution is stored at 4° C. The assay was run as follows:

Membrane #1 (blank) was washed with 5 mL of PBS containing radioactive cadmium. The membrane was then washed twice with 10 mL of non-radioactive, metal free PBS.

Membrane #2 was washed first with 5 mL of MT solution and then 5 mL of PBS containing radioactive cadmium. The membrane was then washed twice with 10 mL of non-radioactive, metal free PBS.

Membrane #3 was washed with 5 mL of BSA solution (7 µg/mL) and then 5 mL of PBS containing radioactive cadmium. The membrane was then washed twice with 10 mL of non-radioactive, metal-free PBS.

Membrane #4 was washed with 10 mL of BSA solution (100 µg/mL) and then 5 mL of PBS containing radioactive cadmium. The membrane was then washed twice with 10 mL of non-radioactive, metal-free PBS.

The results of these experiments are shown below in Table 4.

TABLE 4

| Sample | | CPM |
|---|---|---|
| Membrane 1 | No MT | 174 |
| Membrane 2 | MT (5 mL) | 1171 |
| Membrane 3 | BSA (5 mL of 7 µg/mL) | 77 |
| Membrane 4 | BSA (10 mL of 100 µg/mL) | 151* |

*this membrane was tested a different day where the MT binding activity was greater than 3000 CPM.

Figure 5:
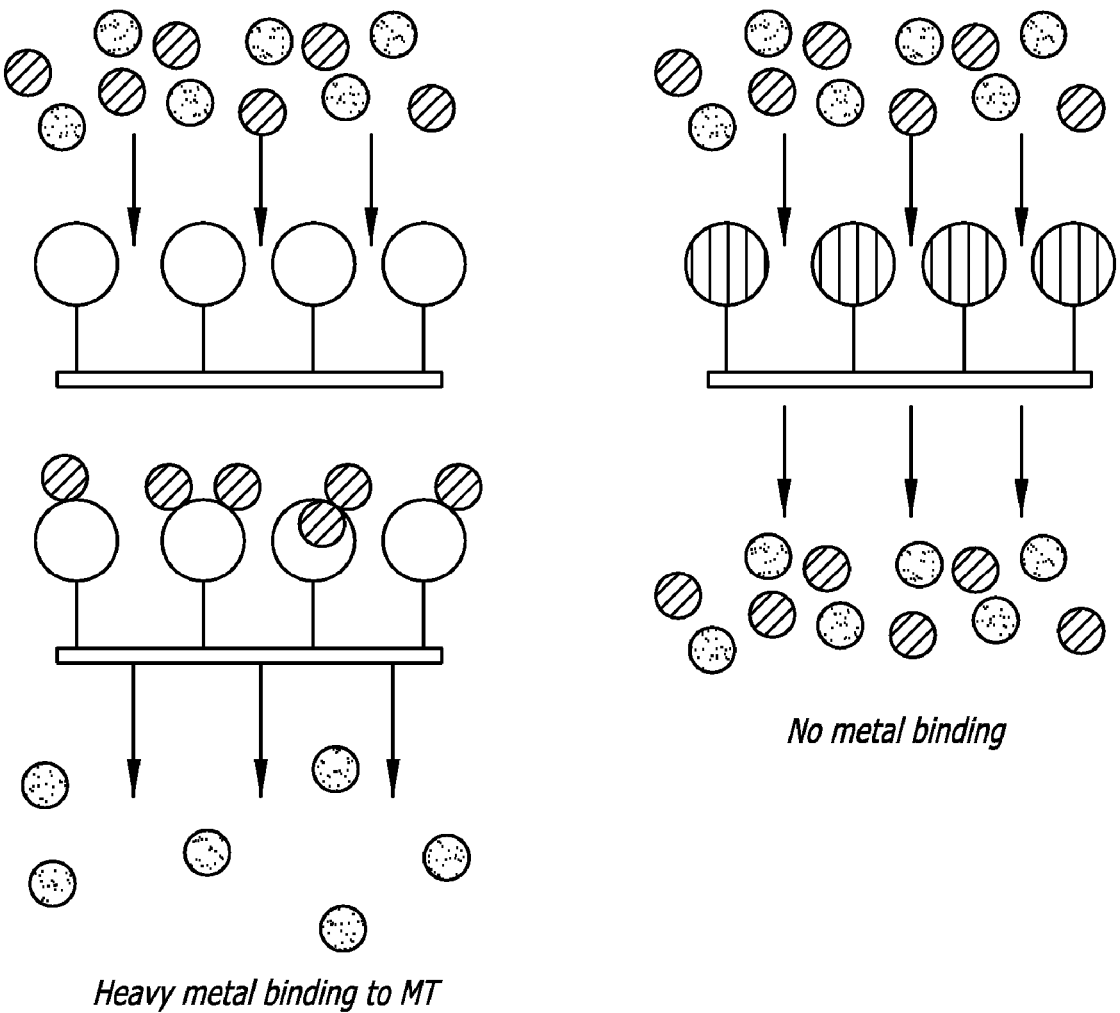
FIG. 5 illustrates the selectivity and affinity of the present invention for binding heavy metals.

Under these experimental conditions, BSA does not remove metal from aqueous solutions, even when using a 10-fold higher concentration of BSA than MT to prepare the membrane. This experiment demonstrates the utility of membrane bound MT for remediation of metal from water or other aqueous substrates (FIG. 5).

Effect of Temperature on Metal Binding Activity.

These binding experiments were performed with Biodyne A membranes.

Membrane #1 (blank) was washed with 5 mL of PBS containing radioactive cadmium. The membrane was then washed twice with 10 mL of non-radioactive, metal-free PBS.

Membrane #2 was washed with 10 mL of MT solution and then 5 mL of PBS containing radioactive cadmium pre-warmed to 60° C. The membrane was then washed twice with 10 mL of non-radioactive, metal-free PBS pre-warmed to 60° C.

Membrane #3 was washed with 10 mL of MT solution and then 5 mL of PBS containing radioactive cadmium cooled to 4° C. The membrane was then washed twice with 10 mL of non-radioactive, metal free PBS cooled to 4° C.

The results of these experiments are shown below in Table 5.

TABLE 5

| Sample | CPM |
|---|---|
| Membrane #1 | 139 |
| Membrane #2 | 3886 |
| Membrane #3 | 2672 |

EXAMPLE 4

Comparison of Rabbit and *Artemia* MT

Metal remediation with the MT proteins of the present invention can be accomplished using metallothionein proteins from a variety of sources. Rabbit liver MT was obtained as a lyophilized protein (Sigma) and solubilized in 400 µL of 50 mM Tris, pH 8.0, 0.001 M DTT to a final concentration of 2.5 mg/mL (rabbit MT stock solution). *Artemia* MT was purified as described supra in Example 1.

Membranes were prepared having bound *Artemia* MT or rabbit liver MT by passing an MT-containing solution through the membrane, as described supra in Example 1. Three membranes, a blank, a membrane bound with *Artemia* MT and a membrane bound with rabbit liver MT, were then placed in a 13 mm fritted glass filtering unit and 10 mL of a metal binding solution (a stock solution of 9000 cpm of $^{109}Cd/25$ µL of solution diluted to 75 µL/10 mL PBS to form the metal binding solution) was passed through the membrane under vacuum. The membrane was then washed three times in PBS, and the membrane-bound radioactivity was measured in a Packard gamma counter. In a second experiment, a larger quantity of *Artemia* MT was bound to the membrane. The results of these two experiments are found in Tables 6 and 7.

TABLE 6

| Sample | | CPM |
|---|---|---|
| Membrane 1 | Blank | 351 |
| Membrane 2 | *Artemia* (20 mL bound to the membrane | 685 |
| Membrane 3 | Rabbit (25 µL of a 2.5 mg/mL solution | 985 |

TABLE 7

| Sample | | CPM |
|---|---|---|
| Membrane 1 | Blank | 231 |
| Membrane 2 | *Artemia* (25 mL bound to the membrane | 980 |

Membrane-bound metallothionein, regardless of source, provides removal of metals from aqueous solutions. In addition, the metal binding activity is a function of the amount of protein applied to the membrane and increasing the amount of MT protein on the membrane results in increased metal binding activity by the membrane.

EXAMPLE 5

Binding of Thimerosal to Metallothionein

Figure 10:
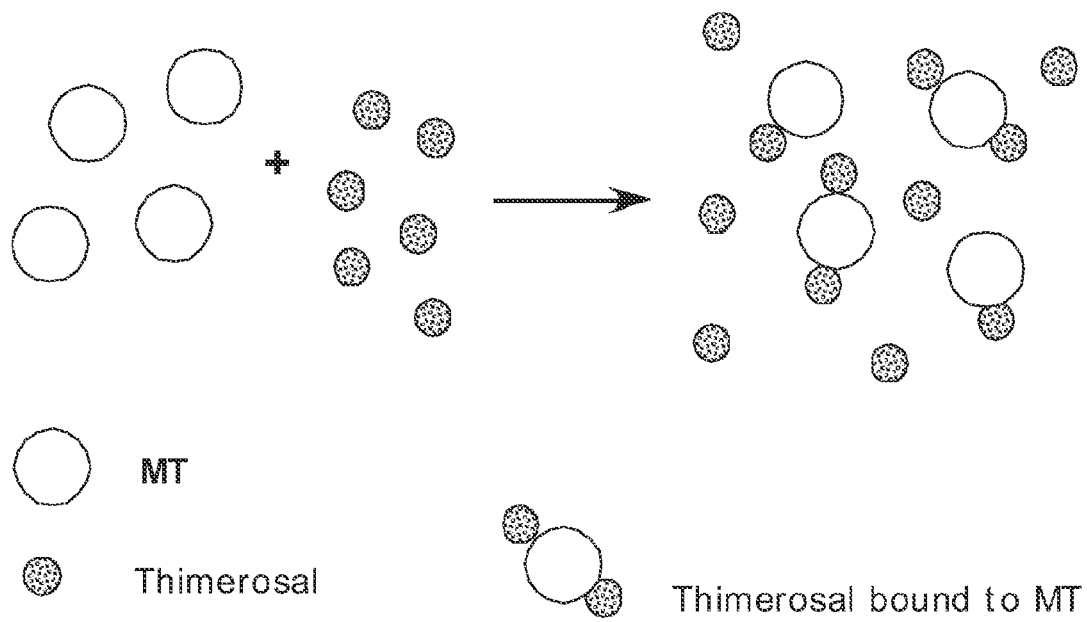
FIG. 10 depicts the formation of metallothionein/thimerosal complexes according to the teachings of the present invention

The binding of thimerosal (or the ethyl mercury from thimerosal) to MT was verified by incubating metallothionein with thimerosal (FIG. 10) and then fractionating the thimerosal/metallothionein complex from unbound thimerosal by molecular exclusion chromatography.

Figure 11:
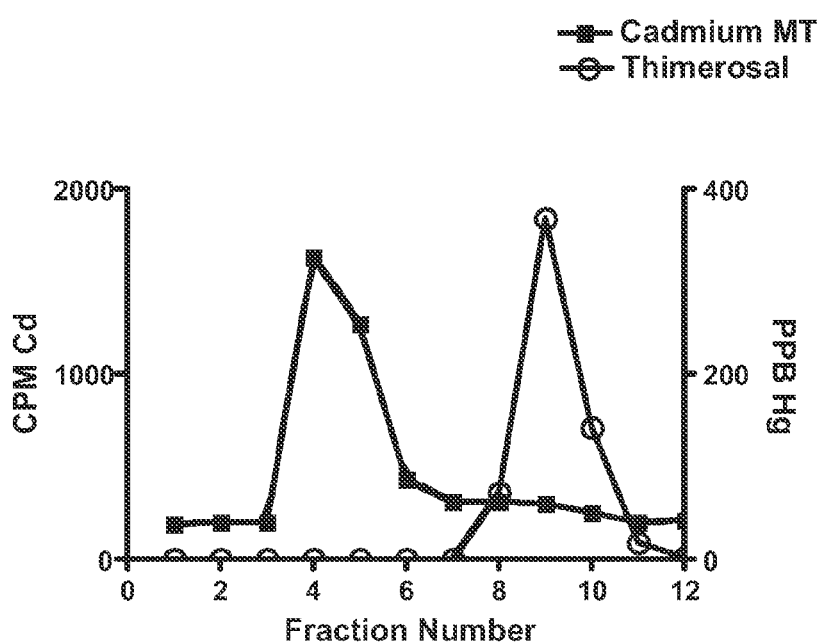
FIG. 11 depicts the elution profile of metallothionein and thimerosal from a chromatography column according to the teachings of the present invention.

Rabbit liver MT (Sigma) was solubilized in 10 mM Tris, pH 8.0 to a final concentration of 1 mg/mL. Recombinant *Artemia* MT was produced in bacteria and extracted by sonication in 10 mM Tris, pH 8.0, 0.1 mM DTT, and 0.5 mM of PMSF. The bacterial extract was placed in boiling water for 10 minutes. The resulting precipitate was collected by centrifugation. The supernatant containing *Artemia* MT was incubated with $^{109}Cd$ and fractionated on a G-50 molecular exclusion column with 50 mM Tris, pH 8.0. Peak metal binding fractions were collected, pooled, and fractionated by FPLC on a Superdex column using Dulbecco's Phosphate Buffered Saline, pH 7.5, with 0.1 mM DTT as elution buffer (D-PBS). The concentration of the purified *Artemia* MT was 206 µg/mL. Thimerosal (Sigma) was solubilzed to a final concentration of 10 mg/mL in D-PBS. Five milliliter polyacrylamide desalting columns were used to fractionate MT bound thimerosal from unbound thimerosal. Metallothionein, and molecules bound thereto, elutes in the void volume ($v_0$) of the column, well ahead of the smaller, unbound thimerosal. In order to calibrate the column, i.e., determine the $v_0$, purified *Artemia* MT (or rabbit MT) was radiolabeled with $^{109}$Cd. The columns were first washed with 10.5 mL of PBS, followed by 1.0 mL of PBS/5 mM EDTA, and then 14 mL of D-PBS. Four hundred microliters of the labeled *Artemia* MT was applied to the surface of a desalting column and allowed to enter the gel by gravity. The protein was eluted from the column with D-PBS. One-half mL fractions were collected from the column and analyzed for radioactivity on a Packard Gamma Counter. The MT eluted from the column (the $v_0$) in fractions four and five. The procedure was repeated with thimerosal to determine where unbound thimerosal would elute from the column. Two micrograms of thimerosal was added to 400 µL of D-PBS. The entire sample was fractionated on a desalting column exactly as described above. Thimerosal was measured by assaying for mercury. The thimerosal eluted from the column in fractions 8 through 10. The results are depicted in FIG. 11.

Figure 12:
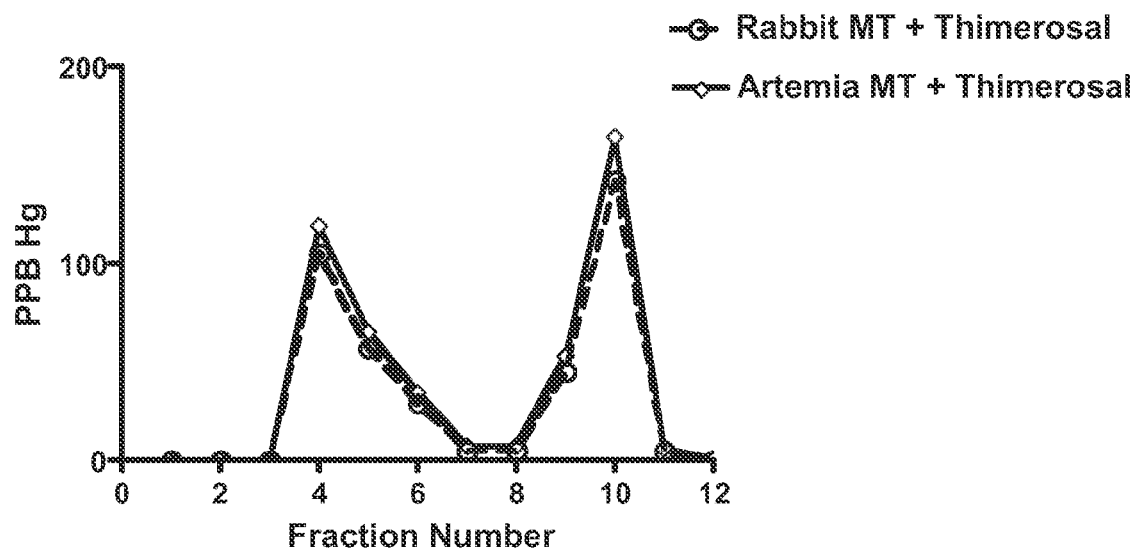
FIG. 12 depicts the elution profile of a mixture of metallothionein and thimerosal from a chromatography column according to the teachings of the present invention.

Next, rabbit liver MT was diluted to 200 µg/mL with 10 mM Tris, pH 8.0. One microgram of thimerosal was pre-incubated with 400 µl of either the rabbit liver MT or the recombinant *Artemia* MT. The mixtures were then fractionated on a polyacrylamide desalting column as described above and the fractions were assayed for mercury. The results of the chromatography is depicted in FIG. 12. Therefore, MT is capable of binding thimerosal in solvents and conditions used to manufacture/store vaccines, i.e., PBS, pH 7.5.

Figure 13:
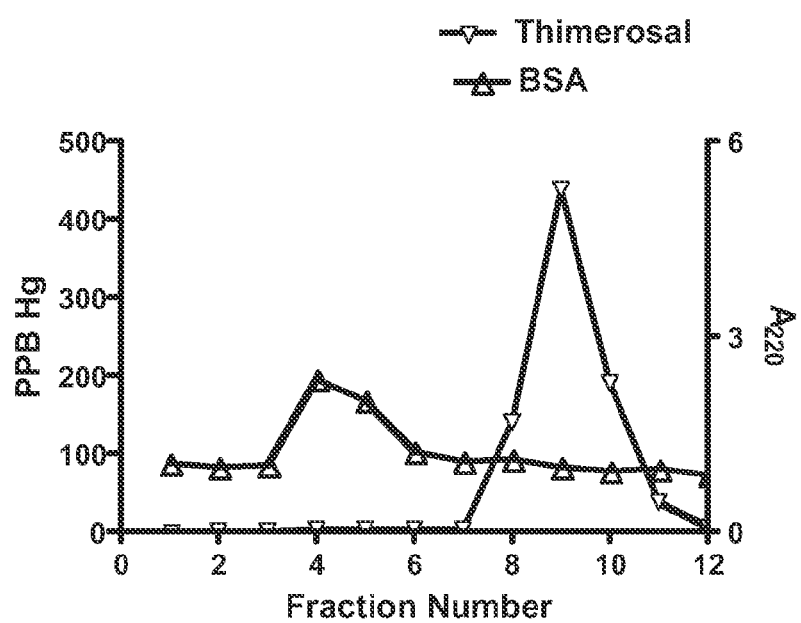
FIG. 13 depicts the elution profile of bovine serum albumin and thimerosal from a chromatography column according to the teachings of the present invention.

Regardless of the source of MT, nearly 50% of the measurable thimerosal was bound to the MT. There was no detectable mercury in the solution of MT, i.e., the only source of the metal was from the thimerosal. In order to show specificity of the MT for thimerosal and the high binding affinity between the two, the experiment was repeated exactly as described above except for substituting with bovine serum albumin (BSA) for the MT. Bovine serum albumin is a known metal binding protein. Elution of BSA from the column was monitored by measuring the absorbance of each fraction at 220 nm. The results of this experiment are shown in FIG. 13. Thimerosal did not bind to BSA in appreciable amounts under these conditions.

EXAMPLE 6

Thimerosal Binding to Membrane-bound Metallothionein

Experiments were conducted to demonstrate that preformed MT/thimerosal complexes could be removed from a solution by filtration though a membrane filter and that MT bound to a membrane filter could be used to remove thimerosal from a solution.

Rabbit liver MT was used for these experiments. The protein was solubilized in 10 mM Tris, pH 8.0, to a final concentration of 1 mg/mL. Millipore Immobilon—P$^{sq}$ PVDF transfer membrane was used as the solid support for these experiments (0.2 µm). The membrane was cut into 1 cm$^2$ pieces and the individual membrane squares were wetted just prior to use by placing them in 100% methanol for 3 seconds, then immersing them in water for two minutes, and finally equilibrating them in 10 mM Tris, pH 8.0 for three minutes. Three different membrane samples were used.

Membrane I—A 1 cm$^2$ piece of membrane was placed in a 10 mL Millipore glass frit filtering unit. Five milliliters of a solution of thimerosal (200 ppb) was passed through the membrane under vacuum. The flow through was collected and analyzed for mercury. This assay served as the control to monitor the efficiency of thimerosal removal from a solution in the assays listed below.

Membrane II—A 1 cm$^2$ piece of membrane was placed in a 10 mL Millipore glass frit filtering unit. Five milliliters of a solution of rabbit liver MT (0.04 mg/mL, 200 µg total protein in 10 mM Tris, pH 8.0) was passed through the membrane under vacuum. This was followed by passing 5 mL of a solution of 200 PPB thimerosal in 10 mM Tris, pH 8.0 through the membrane under vacuum. The flow through was collected and analyzed for mercury. This assay was designed to show that MT immobilized on a permeable membrane was capable of removing thimerosal from a solution passing through the membrane.

Membrane III—A 1 cm$^2$ piece of membrane was placed in a 10 mL Millipore glass frit filtering unit. One microliter (1 µl) of thimerosal (1 µg/µl in 10 mM Tris, pH 8.0) was mixed with 200 µg of MT (200 µl of the 1 mg/mL stock solution). The solution was diluted to a final volume of 5 mL with 10 mM Tris, pH 8.0 to give a final thimerosal concentration of 200 PPB. The MT/thimerosal mixture was then passed through the membrane. The flow through was collected and analyzed for mercury. This assay was designed to show that thimerosal could be removed from a solution by first reacting a thimerosal-containing solution with MT to generate MT/thimerosal complexes and then removing the complexes from the solution by passing the solution through a permeable membrane with a high binding affinity for protein. The results of this experiment are shown in Table 8 below.

TABLE 8

| Membrane | Thimerosal (PPB) | % Thimerosal removed |
| --- | --- | --- |
| Thimerosal Solution | 148 | — |
| Membrane I (No MT) | 138 | 6.7% |
| Membrane II (MT) | 94 | 36.5% |
| Membrane III (MT/Thimerosal) | 127 | 14.2% |

The results of this experiment demonstrate that MT bound to a permeable membrane is capable of removing thimerosal from a solution passing through the membrane. Additionally, thimerosal can be removed from a solution by first adding MT to the solution containing thimerosal to form MT/thimerosal complexes and then collecting the complexes by passing the solution through a permeable membrane or some other device form for capture of the MT/thimerosal complexes.

In closing it is to be understood that the embodiments of the invention disclosed herein are illustrative of the principals of the invention. Other modifications may be employed which are within the scope of the invention and accordingly, the present invention is not limited to that precisely as shown and described in the present specification.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on those embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are individually incorporated by reference herein in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A device for the removal of thimerosal from a medication to be administered to a subject comprising:
a dosing device having associated therewith at least one substantially purified metallothionein protein, wherein said at least one substantially purified metallothionein protein binds said thimerosal from said medication resulting in a substantially thimerosal-free medication.

2. The device of claim 1 wherein said dosing device is selected from the group consisting of syringes, oral dosing syringes, oral dosing cups, inhalation devices, needles, needleless injection devices and opthalmologic administrative devices.

3. The device of claim 1 wherein said medication is selected from the group consisting of vaccines, immunogenic compositions, liquid pharmaceutical compositions, colloidal pharmaceutical compositions, suspension pharmaceutical compositions, aerosols and dry powders.

4. The device of claim 1 wherein said administration comprises a route of administration selected from the group consisting of intravenous injection, subcutaneous injection, intradermal injection, intramuscular injection, intravenous infusion, oral, inhalation, and intraocular.

5. The device of claim 1 wherein said dosing device provides a sterile environment.

6. The device of claim 1 wherein said dosing device removes thimerosal from said medication proximal in time to said administration.

7. The device of claim 1 wherein at least one interior surface of said dosing device has at least one substantially pure metallothionein protein coated thereon.

8. The device of claim 7 wherein said at least one substantially pure metallothionein protein is covalently linked to said interior surface.

9. The device of claim 7 wherein said at least one substantially pure metallothionein protein is coated on said interior surface in a polymeric coating.

10. The device of claim 1 wherein said at least one substantially pure metallothionein protein is bound to a solid support, said solid support associated with said dosing device.

11. The device of claim 10 wherein said at least one substantially pure metallothionein protein is bound to a solid support, said solid support disposed within said dosing device.

12. The device of claim 7 wherein said solid support is selected from the group consisting of filters, membranes, nanoparticles, beads, solid support particulates, and polymer coatings.

13. The device of claim 12 wherein said at least one substantially pure metallothionein protein is associated with a plurality of beads or nanoparticles, said plurality of beads or nanoparticles disposed within said dosing device.

14. The device of claim 12 wherein said solid support comprises a biocompatible polymer.

15. The device of claim 14 wherein said biocompatible polymer is selected from the group consisting of fluorinated polymers, polyolefins, polystyrene, substituted polystyrenes, polysulfones, polyesters, polyacrylates, polycarbonates; vinyl polymers, copolymers of butadiene and styrene, fluorinated ethylene-propylene copolymers, ethylenechlorotrifluoroethylene copolymers, nylon and mixtures thereof.

16. The device of claim 12 wherein said solid support is a filter.

17. The device of claim 1 wherein said at least one substantially purified metallothionein (MT) protein, or a portion thereof, is from an organism selected from the group consisting of mammals, fish, mollusks, echinoderms, crustaceans, reptiles, nematodes, grains, plants, yeast, and fungi.

18. The device according to claim 17 wherein said mammal is a human.

19. The device according to claim 17 wherein said mammal is a rabbit.

20. The device according to claim 17 wherein said crustacean is brine shrimp (*Artemia*).

21. The device of claim 1 wherein said MT protein has an amino acid sequence selected from the group consisting of SEQ ID NO. 2, SEQ ID NO. 4, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 21 and SEQ ID NO. 23.

22. A method of removing thimerosal from a medication to be administered to a subject comprising:
   contacting a thimerosal-containing medication with at least one substantially purified metallothionein protein associated with a dosing device; and
   administering the resulting substantially thimerosal-free medication to said subject.

23. A system for removing thimerosal from a medication to be administered to a subject comprising:
   a device having at least one metallothionein protein associated therewith;
   wherein passage of a medication through said device results in binding of said thimerosal to said metallothionein protein and a substantially thimerosal-free medication.

24. A device for the removal of thimerosal from a medication to be administered to a subject comprising:
   a solid support associated with at least one substantially purified metallothionein protein, wherein said at least one substantially purified metallothionein protein binds said thimerosal from said medication resulting in a substantially thimerosal-free medication.

* * * * *

UNITED STATES PATENT AND TRADEMARK OFFICE
CERTIFICATE OF CORRECTION

PATENT NO. : 7,767,872 B2  
APPLICATION NO. : 11/624059  
DATED : August 3, 2010  
INVENTOR(S) : Roger A. Acey et al.

It is certified that error appears in the above-identified patent and that said Letters Patent is hereby corrected as shown below:

On the title page, item [73]:

Assignee: replace "MPG Biotechnologies, LLC" with --MGP Biotechnologies, LLC--

Column 38, line 21, replace second occurrence of "SEQ ID NO. 21" with --SEQ ID NO. 22--

Signed and Sealed this
Eighth Day of May, 2012

David J. Kappos
*Director of the United States Patent and Trademark Office*

SEQUENCE LISTING

<160> NUMBER OF SEQ ID NOS: 24

<210> SEQ ID NO 1
<211> LENGTH: 147
<212> TYPE: DNA
<213> ORGANISM: Artemia sp.

<400> SEQUENCE: 1

```
atggactgct gcaagaacgg ttgcacctgt gccccaaatt gcaaatgtgc caaagactgc      60
aaatgctgca aaggttgtga gtgcaaaagc aacccagaat gcaaatgtga gaagaactgt     120
tcatgcaact catgtggttg tcactga                                         147
```

<210> SEQ ID NO 2
<211> LENGTH: 48
<212> TYPE: PRT
<213> ORGANISM: Artemia sp.

<400> SEQUENCE: 2

```
Met Asp Cys Cys Lys Asn Gly Cys Thr Cys Ala Pro Asn Cys Lys Cys
 1               5                  10                  15

Ala Lys Asp Cys Lys Cys Cys Lys Gly Cys Glu Cys Lys Ser Asn Pro
            20                  25                  30
```

Glu Cys Lys Cys Glu Lys Asn Cys Ser Cys Asn Ser Cys Gly Cys His
        35                  40                  45

<210> SEQ ID NO 3
<211> LENGTH: 66
<212> TYPE: DNA
<213> ORGANISM: Artemia sp.

<400> SEQUENCE: 3
atggactgct gcaagaacgg ttgcacctgt gccccaaatt gcaaatgtgc caaagactgc    60
aaatgc                                                              66

<210> SEQ ID NO 4
<211> LENGTH: 22
<212> TYPE: PRT
<213> ORGANISM: Artemia sp.

<400> SEQUENCE: 4

Met Asp Cys Cys Lys Asn Gly Cys Thr Cys Ala Pro Asn Cys Lys Cys
1               5                   10                  15

Ala Lys Asp Cys Lys Cys
            20

<210> SEQ ID NO 5
<211> LENGTH: 34
<212> TYPE: DNA
<213> ORGANISM: Artificial
<220> FEATURE:
<223> OTHER INFORMATION: 5' primer (N-terminal side) designated MT-Not I
      for PCR amplification of Artemia metal binding protein sequences

<400> SEQUENCE: 5
acctatgcgg ccgcaaatgg actgctgcaa gaac                               34

<210> SEQ ID NO 6
<211> LENGTH: 31
<212> TYPE: DNA
<213> ORGANISM: Artificial
<220> FEATURE:
<223> OTHER INFORMATION: 3' primer (C-terminal side) designated dT-Not I
      for PCR amplification of Artemia metal binding protein sequences

<400> SEQUENCE: 6
gcaccaacta gtgcctttttt tttttttttt a                                 31

<210> SEQ ID NO 7
<211> LENGTH: 31
<212> TYPE: DNA
<213> ORGANISM: Artificial
<220> FEATURE:
<223> OTHER INFORMATION: 3' primer (C-terminal side) designated dT-Not I
      for PCR amplification of Artemia metal binding protein sequences

<400> SEQUENCE: 7
gcaccaacta gtgcctttttt tttttttttt c                                 31

<210> SEQ ID NO 8
<211> LENGTH: 31
<212> TYPE: DNA
<213> ORGANISM: Artificial
<220> FEATURE:
<223> OTHER INFORMATION: 3' primer (C-terminal side) designated dT-Not I
      for PCR amplification of Artemia metal binding protein sequences

<400> SEQUENCE: 8
gcaccaacta gtgccttttt tttttttttt g         31

<210> SEQ ID NO 9
<211> LENGTH: 33
<212> TYPE: DNA
<213> ORGANISM: Artificial
<220> FEATURE:
<223> OTHER INFORMATION: 5' primer containing an Nde I site

<400> SEQUENCE: 9
gctacacata tgtccatgga ctgctgcaag aac         33

<210> SEQ ID NO 10
<211> LENGTH: 31
<212> TYPE: DNA
<213> ORGANISM: Artificial
<220> FEATURE:
<223> OTHER INFORMATION: 3' primer containing Sal I site

<400> SEQUENCE: 10
acgaacgtcg acgccttttt tttttttttt a         31

<210> SEQ ID NO 11
<211> LENGTH: 48
<212> TYPE: PRT
<213> ORGANISM: Artemia sp.

<400> SEQUENCE: 11

Met Asp Cys Cys Lys Asn Gly Cys Thr Cys Ala Pro Asn Cys Lys Cys
1               5                   10                  15

Ala Lys Asp Cys Lys Cys Lys Gly Cys Glu Cys Lys Ser Asn Pro
            20                  25                  30

Glu Cys Lys Cys Glu Lys Asn Cys Ser Cys Asn Ser Cys Gly Cys His
        35                  40                  45

<210> SEQ ID NO 12
<211> LENGTH: 61
<212> TYPE: PRT
<213> ORGANISM: Oryctolagus cuniculus

<400> SEQUENCE: 12

Met Asp Pro Asn Cys Ser Cys Ala Thr Arg Asp Ser Cys Ala Cys Ala
1               5                   10                  15

Ser Ser Cys Lys Cys Lys Glu Cys Lys Cys Thr Ser Cys Lys Lys Ser
            20                  25                  30

Cys Cys Ser Cys Cys Pro Ala Gly Cys Thr Lys Cys Ala Gln Gly Cys
        35                  40                  45

Ile Cys Lys Gly Ala Leu Asp Lys Cys Ser Cys Cys Ala
    50                  55                  60

<210> SEQ ID NO 13
<211> LENGTH: 61
<212> TYPE: PRT
<213> ORGANISM: Homo sapiens

<400> SEQUENCE: 13

Met Asp Pro Asn Cys Ser Cys Ala Ala Gly Asp Ser Cys Thr Cys Ala
1               5                   10                  15

Gly Ser Cys Lys Cys Lys Glu Cys Lys Cys Thr Ser Cys Lys Lys Ser
            20                  25                  30

```
Cys Cys Ser Cys Cys Pro Val Gly Cys Ala Lys Cys Ala Gln Gly Cys
        35                  40                  45

Ile Cys Lys Gly Ala Ser Asp Lys Cys Ser Cys Ala
50                  55                  60

<210> SEQ ID NO 14
<211> LENGTH: 61
<212> TYPE: PRT
<213> ORGANISM: Cercopithecus aethiops

<400> SEQUENCE: 14

Met Asp Pro Asn Cys Ser Cys Ala Thr Gly Val Ser Cys Thr Cys Ala
1               5                   10                  15

Asp Ser Cys Lys Cys Lys Glu Cys Lys Cys Thr Ser Cys Lys Lys Ser
            20                  25                  30

Cys Cys Ser Cys Cys Pro Val Gly Cys Ala Lys Cys Ala Gln Gly Cys
        35                  40                  45

Val Cys Lys Gly Ala Ser Glu Lys Cys Asn Cys Ala
50                  55                  60

<210> SEQ ID NO 15
<211> LENGTH: 60
<212> TYPE: PRT
<213> ORGANISM: Ictalurus punctatus

<400> SEQUENCE: 15

Met Asp Pro Cys Glu Cys Ser Lys Thr Gly Thr Cys Asn Cys Gly Thr
1               5                   10                  15

Ser Cys Lys Cys Ser Asn Cys Gln Cys Ala Cys Cys Lys Lys Ser Cys
            20                  25                  30

Cys Ser Cys Cys Pro Ser Gly Cys Ser Lys Cys Ala Ser Gly Cys Val
        35                  40                  45

Cys Lys Gly Asp Thr Cys Asp Ser Lys Cys Cys Gln
50                  55                  60

<210> SEQ ID NO 16
<211> LENGTH: 62
<212> TYPE: PRT
<213> ORGANISM: Xenopus laevis

<400> SEQUENCE: 16

Met Asp Pro Gln Asp Cys Lys Cys Glu Thr Gly Ala Ser Cys Ser Cys
1               5                   10                  15

Gly Thr Thr Cys Ser Cys Ser Asn Cys Lys Cys Thr Ser Cys Lys Lys
            20                  25                  30

Ser Cys Cys Ser Cys Cys Pro Ala Glu Cys Ser Lys Cys Ser Gln Gly
        35                  40                  45

Cys His Cys Glu Lys Gly Ser Lys Lys Cys Ser Cys Asn
50                  55                  60

<210> SEQ ID NO 17
<211> LENGTH: 71
<212> TYPE: PRT
<213> ORGANISM: Mytilus edulis

<400> SEQUENCE: 17

Pro Gly Pro Cys Asn Cys Ile Glu Thr Asn Val Cys Ile Cys Gly Thr
1               5                   10                  15

Gly Cys Ser Gly Lys Cys Cys Arg Cys Gly Asp Ala Cys Lys Cys Ala
            20                  25                  30
```

```
Ser Gly Cys Gly Cys Ser Gly Cys Lys Val Val Cys Lys Cys Ser Gly
        35                  40                  45

Thr Cys Lys Cys Gly Cys Asp Cys Thr Gly Pro Thr Asn Cys Lys Cys
    50                  55                  60

Glu Ser Gly Cys Ser Cys Lys
65                  70

<210> SEQ ID NO 18
<211> LENGTH: 68
<212> TYPE: PRT
<213> ORGANISM: Lytechinus pictus

<400> SEQUENCE: 18

Met Pro Gly Pro Asp Val Lys Cys Phe Cys Arg Asp Gly Lys Glu
1               5                   10                  15

Cys Ala Cys Gly Gly Gly Glu Cys Cys Ile Thr Gly Lys Cys Cys Lys
            20                  25                  30

Glu Gly Asp Arg Thr Cys Cys Gly Lys Cys Ser Asn Ala Ala Cys Lys
        35                  40                  45

Cys Ala Asp Gly Cys Lys Cys Glu Gly Ala Cys Ala Cys Thr Met Gly
    50                  55                  60

Asn Cys Thr Cys
65

<210> SEQ ID NO 19
<211> LENGTH: 43
<212> TYPE: PRT
<213> ORGANISM: Drosophila melanogaster

<400> SEQUENCE: 19

Met Val Cys Lys Gly Cys Gly Thr Asn Cys Gln Cys Ser Ala Gln Lys
1               5                   10                  15

Cys Gly Asp Asn Cys Ala Cys Asn Lys Asp Cys Gln Cys Val Cys Lys
            20                  25                  30

Asn Gly Pro Lys Asp Gln Cys Cys Ser Asn Lys
        35                  40

<210> SEQ ID NO 20
<211> LENGTH: 62
<212> TYPE: PRT
<213> ORGANISM: Caenorhabditis elegans

<400> SEQUENCE: 20

Val Cys Lys Cys Asp Cys Lys Asn Gln Asn Cys Ser Cys Asn Thr Gly
1               5                   10                  15

Thr Lys Asp Cys Asp Cys Ser Asp Ala Lys Cys Cys Glu Gln Tyr Cys
            20                  25                  30

Cys Pro Thr Ala Ser Glu Lys Lys Cys Cys Lys Ser Gly Cys Ala Gly
        35                  40                  45

Gly Cys Lys Cys Ala Asn Cys Glu Cys Ala Gln Ala Ala His
    50                  55                  60

<210> SEQ ID NO 21
<211> LENGTH: 74
<212> TYPE: PRT
<213> ORGANISM: Oryza sativa

<400> SEQUENCE: 21

Met Ser Cys Ser Cys Gly Ser Ser Cys Ser Cys Gly Ser Asn Cys Ser
1               5                   10                  15
```

-continued

```
Cys Gly Lys Lys Tyr Pro Asp Leu Glu Glu Lys Ser Ser Ser Thr Lys
             20                  25                  30

Ala Thr Val Val Leu Gly Val Ala Pro Glu Lys Lys Ala Gln Gln Phe
             35                  40                  45

Glu Ala Ala Glu Ser Gly Thr Ala His Gly Cys Ser Cys Gly
    50                  55                  60

Ser Ser Cys Arg Cys Asn Pro Cys Asn Cys
65                  70

<210> SEQ ID NO 22
<211> LENGTH: 75
<212> TYPE: PRT
<213> ORGANISM: Triticum aestivum

<400> SEQUENCE: 22

Met Ser Cys Asn Cys Gly Ser Gly Cys Ser Cys Gly Ser Asp Cys Lys
1               5                   10                  15

Cys Gly Lys Met Tyr Pro Asp Leu Thr Glu Gln Gly Ser Ala Ala Ala
             20                  25                  30

Gln Val Ala Ala Val Val Leu Gly Val Ala Pro Glu Asn Lys Ala
             35                  40                  45

Gly Gln Phe Glu Val Ala Ala Gly Gln Ser Gly Glu Gly Cys Ser Cys
    50                  55                  60

Gly Asp Asn Cys Lys Cys Asn Pro Cys Asn Cys
65                  70                  75

<210> SEQ ID NO 23
<211> LENGTH: 62
<212> TYPE: PRT
<213> ORGANISM: Candida glabrata

<400> SEQUENCE: 23

Ala Asn Asp Cys Lys Cys Pro Asn Gly Cys Ser Cys Pro Asn Cys Ala
1               5                   10                  15

Asn Gly Gly Cys Gln Cys Gly Asp Lys Cys Glu Cys Lys Lys Gln Ser
             20                  25                  30

Cys His Gly Cys Gly Glu Gln Cys Lys Cys Gly Ser His Gly Ser Ser
             35                  40                  45

Cys His Gly Ser Cys Gly Cys Gly Asp Lys Cys Glu Cys Lys
             50                  55                  60

<210> SEQ ID NO 24
<211> LENGTH: 9
<212> TYPE: PRT
<213> ORGANISM: Artificial
<220> FEATURE:
<223> OTHER INFORMATION: Linker peptide

<400> SEQUENCE: 24

Ser Ser Gly Gly Gly Gly Ser Asp Ile
1               5
```